(12) United States Patent
Binch et al.

(10) Patent No.: US 8,410,132 B2
(45) Date of Patent: Apr. 2, 2013

(54) MODULATORS OF CYSTIC FIBROSIS TRANSMEMBRANE CONDUCTANCE REGULATOR

(75) Inventors: Hayley Binch, Encinitas, CA (US); Peter D. J. Grootenhuis, San Diego, CA (US); Sara S Hadida Ruah, La Jolla, CA (US); Jinglan Zhou, San Diego, CA (US); Anna Hazlewood, San Diego, CA (US); Lev T. D. Fanning, San Marcos, CA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 13/453,193

(22) Filed: Apr. 23, 2012

(65) Prior Publication Data
US 2013/0018070 A1    Jan. 17, 2013

Related U.S. Application Data

(60) Division of application No. 12/722,642, filed on Mar. 12, 2010, now Pat. No. 8,188,283, which is a continuation of application No. PCT/US2008/076376, filed on Sep. 15, 2008.

(60) Provisional application No. 60/972,599, filed on Sep. 14, 2007.

(51) Int. Cl.
*A61K 31/4375* (2006.01)
*A61P 3/10* (2006.01)
*A61P 5/18* (2006.01)
*A61P 11/00* (2006.01)
*A61P 25/16* (2006.01)
*A61P 25/28* (2006.01)
*C07D 471/04* (2006.01)
*C12N 5/00* (2006.01)
*C07K 1/00* (2006.01)

(52) U.S. Cl. ......... 514/300; 435/375; 530/402; 546/123

(58) Field of Classification Search .......................... None
See application file for complete search history.

(56) References Cited

U.S. PATENT DOCUMENTS

| 5,225,418 A | 7/1993 | Miller |
| 2007/0060577 A1 | 3/2007 | Player et al. |

FOREIGN PATENT DOCUMENTS

| DE | 19532235 A1 | 3/1997 |
| EP | 0366193 A2 | 5/1990 |
| WO | 93/23040 | 11/1993 |
| WO | 93/23041 | 11/1993 |
| WO | 97/04775 | 2/1997 |
| WO | 2004/080971 | 9/2004 |
| WO | 2006/002421 | 1/2006 |
| WO | 2006/034113 | 3/2006 |
| WO | 2006/047415 | 5/2006 |
| WO | 2006/050940 | 5/2006 |
| WO | 2006/050942 | 5/2006 |
| WO | 2006/076442 | 7/2006 |
| WO | 2007/033137 | 3/2007 |
| WO | 2007/033232 | 3/2007 |
| WO | 2007/075901 | 7/2007 |

OTHER PUBLICATIONS

Bombieri et al., "Complete mutational screening of the CFTR gene in 120 patients with pulmonary disease" Hum Genet (1998) 103:718-722; Pavia, Italy.
Sloane et al., "A Pharmacolgic Approac to Acquired Cystic Fibrosis Transmembrane Conductance Regulator Dysfunction in Smoking Related Lung Disease" (2012) PLoS One 7(6): e39809. doi:10.1371/journal.pone.0039809; USA.
Levin et al., "CFTR-Regulated Chloride Transport at the Ocular Surface in Living Mice Measured by Potential Differences" Investigative Ophthamology & Visual Science, Apr. 2005, vol. 46, No. 4, San Francisco/USA.
PCT/US2008/076376 International Search Report.

*Primary Examiner* — Janet Andres
*Assistant Examiner* — Timothy R Rozof
(74) *Attorney, Agent, or Firm* — Nancy K. Brennan

(57) ABSTRACT

The present invention relates to modulators of ATP-Binding Cassette ("ABC") transporters or fragments thereof, including Cystic Fibrosis Transmembrane Conductance Regulator, compositions thereof, and methods therewith. The present invention also relates to methods of treating ABC transporter mediated diseases using such modulators.

7 Claims, No Drawings

MODULATORS OF CYSTIC FIBROSIS TRANSMEMBRANE CONDUCTANCE REGULATOR

CROSS-REFERENCE TO RELATED APPLICATIONS

The present application is a continuation of International Application No. PCT/US2008/076376 filed Sep. 15, 2008 entitled "MODULATORS OF CYSTIC FIBROSIS TRANSMEMBRANE CONDUCTANCE REGULATOR" which in turn claims the benefit under 35 U.S.C. §119, to U.S. Provisional Application No. 60/972,599, filed Sep. 14, 2007 and entitled "MODULATORS OF CYSTIC FIBROSIS TRANSMEMBRANE CONDUCTANCE REGULATOR," the entire contents of which is incorporated herein by reference.

TECHNICAL FIELD OF THE INVENTION

The present invention relates to modulators of cystic fibrosis transmembrane conductance regulator ("CFTR"), compositions thereof, and methods therewith. The present invention also relates to methods of treating CFTR mediated diseases using such modulators.

BACKGROUND OF THE INVENTION

ABC transporters are a family of membrane transporter proteins that regulate the transport of a wide variety of pharmacological agents, potentially toxic drugs, and xenobiotics, as well as anions. ABC transporters are homologous membrane proteins that bind and use cellular adenosine triphosphate (ATP) for their specific activities. Some of these transporters were discovered as multidrug resistance proteins (like the MDR1-P glycoprotein, or the multidrug resistance protein, MRP1), defending malignant cancer cells against chemotherapeutic agents. To date, 48 ABC Transporters have been identified and grouped into 7 families based on their sequence identity and function.

ABC transporters regulate a variety of important physiological roles within the body and provide defense against harmful environmental compounds. Because of this, they represent important potential drug targets for the treatment of diseases associated with defects in the transporter, prevention of drug transport out of the target cell, and intervention in other diseases in which modulation of ABC transporter activity may be beneficial.

One member of the ABC transporter family commonly associated with disease is the cAMP/ATP-mediated anion channel, CFTR. CFTR is expressed in a variety of cells types, including absorptive and secretory epithelia cells, where it regulates anion flux across the membrane, as well as the activity of other ion channels and proteins. In epithelia cells, normal functioning of CFTR is critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See Gregory, R. J. et al. (1990) Nature 347:382-386; Rich, D. P. et al. (1990) Nature 347:358-362), (Riordan, J. R. et al. (1989) Science 245:1066-1073). A defect in this gene causes mutations in CFTR resulting in cystic fibrosis ("CF"), the most common fatal genetic disease in humans. Cystic fibrosis affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease.

In patients with cystic fibrosis, mutations in CFTR endogenously expressed in respiratory epithelia leads to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, >1000 disease causing mutations in the CF gene have been identified (http://www.genet.sickkids.on.ca/cftr/). The most prevalent mutation is a deletion of phenylalanine at position 508 of the CFTR amino acid sequence, and is commonly referred to as ΔF508-CFTR. This mutation occurs in approximately 70% of the cases of cystic fibrosis and is associated with a severe disease.

The deletion of residue 508 in ΔF508-CFTR prevents the nascent protein from folding correctly. This results in the inability of the mutant protein to exit the ER, and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of ΔF508-CFTR in the membrane are functional, albeit less than wild-type CFTR. (Dalemans et al. (1991), Nature Lond. 354: 526-528; Denning et al., supra; Pasyk and Foskett (1995), J. Cell. Biochem. 270: 12347-50). In addition to ΔF508-CFTR, other disease causing mutations in CFTR that result in defective trafficking, synthesis, and/or channel gating could be up- or down-regulated to alter anion secretion and modify disease progression and/or severity.

Although CFTR transports a variety of molecules in addition to anions, it is clear that this role (the transport of anions) represents one element in an important mechanism of transporting ions and water across the epithelium. The other elements include the epithelial $Na^+$ channel, ENaC, $Na^+/2Cl^-/K^+$ co-transporter, $Na^+$—$K^+$-ATPase pump and the basolateral membrane $K^+$ channels, that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the $Na^+$—$K^+$-ATPase pump and $Cl^-$ channels expressed on the basolateral surface of the cell. Secondary active transport of chloride from the luminal side leads to the accumulation of intracellular chloride, which can then passively leave the cell via $Cl^-$ channels, resulting in a vectorial transport. Arrangement of $Na^+/2Cl^-/K^+$ co-transporter, $Na^+K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

In addition to cystic fibrosis, modulation of CFTR activity may be beneficial for other diseases not directly caused by mutations in CFTR, such as secretory diseases and other protein folding diseases mediated by CFTR. These include, but are not limited to, chronic obstructive pulmonary disease (COPD), dry eye disease, and Sjögren's Syndrome. COPD is characterized by airflow limitation that is progressive and not fully reversible. The airflow limitation is due to mucus hypersecretion, emphysema, and bronchiolitis. Activators of mutant or wild-type CFTR offer a potential treatment of mucus hypersecretion and impaired mucociliary clearance that is common in COPD. Specifically, increasing anion secretion across CFTR may facilitate fluid transport into the airway surface liquid to hydrate the mucus and optimized periciliary fluid viscosity. This would lead to enhanced mucociliary clearance and a reduction in the symptoms associated with COPD. Dry eye disease is characterized by a decrease in tear aqueous production and abnormal tear film lipid, protein and mucin profiles. There are many causes of dry eye, some of which include age, Lasik eye surgery, arthritis, medications, chemical/thermal burns, allergies, and diseases, such as cystic fibrosis and Sjögrens's syndrome. Increasing anion secretion via CFTR would enhance fluid transport from the corneal endothelial cells and secretory glands surrounding the eye to increase corneal hydration. This would help to alleviate the symptoms associated with dry eye disease. Sjögrens's syndrome is an autoimmune disease in which the immune system attacks moisture-producing glands throughout the body, including the eye, mouth, skin, respiratory tissue, liver, vagina, and gut. Symptoms, include, dry eye, mouth, and vagina, as well as lung disease. The disease is also associated with rheumatoid arthritis, systemic lupus, systemic sclerosis, and polymypositis/dermatomyositis. Defective protein trafficking is believed to cause the disease, for which treatment options are limited. Modulators of CFTR activity may hydrate the various organs afflicted by the disease and help to elevate the associated symptoms.

As discussed above, it is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. In fact, this cellular phenomenon of defective ER processing of ABC transporters by the ER machinery, has been shown to be the underlying basis not only for CF disease, but for a wide range of other isolated and inherited diseases. The two ways that the ER machinery can malfunction is either by loss of coupling to ER export of the proteins leading to degradation, or by the ER accumulation of these defective/misfolded proteins [Aridor M, et al., Nature Med., 5(7), pp 745-751 (1999); Shastry, B. S., et al., Neurochem. International, 43, pp 1-7 (2003); Rutishauser, J., et al., Swiss Med Wkly, 132, pp 211-222 (2002); Morello, J P et al., TIPS, 21, pp. 466-469 (2000); Bross P., et al., Human Mut., 14, pp. 186-198 (1999)]. The diseases associated with the first class of ER malfunction are cystic fibrosis (due to misfolded ΔF508-CFTR as discussed above), hereditary emphysema (due to a1-antitrypsin; non Piz variants), hereditary hemochromatosis, hoagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, Mucopolysaccharidoses (due to lysosomal processing enzymes), Sandhof/Tay-Sachs (due to β-hexosaminidase), Crigler-Najjar type II (due to UDP-glucuronyl-sialyctransferase), polyendocrinopathy/hyperinsulemia, Diabetes mellitus (due to insulin receptor), Laron dwarfism (due to growth hormone receptor), myleoperoxidase deficiency, primary hypoparathyroidism (due to preproparathyroid hormone), melanoma (due to tyrosinase). The diseases associated with the latter class of ER malfunction are Glycanosis CDG type 1, hereditary emphysema (due to al-Antitrypsin (PiZ variant), congenital hyperthyroidism, osteogenesis imperfecta (due to Type I, II, IV procollagen), hereditary hypofibrinogenemia (due to fibrinogen), ACT deficiency (due to α1-antichymotrypsin), Diabetes insipidus (DI), neurophyseal DI (due to vasopvessin hormone/V2-receptor), neprogenic DI (due to aquaporin II), Charcot-Marie Tooth syndrome (due to peripheral myelin protein 22), Perlizaeus-Merzbacher disease, neurodegenerative diseases such as Alzheimer's disease (due to PAPP and presenilins), Parkinson's disease, amyotrophic lateral sclerosis, progressive supranuclear plasy, Pick's disease, several polyglutamine neurological disorders such as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease (due to lysosomal α-galactosidase A) and Straussler-Scheinker syndrome (due to Prp processing defect).

In addition to up-regulation of CFTR activity, reducing anion secretion by CFTR modulators may be beneficial for the treatment of secretory diarrheas, in which epithelial water transport is dramatically increased as a result of secretagogue activated chloride transport. The mechanism involves elevation of cAMP and stimulation of CFTR.

Although there are numerous causes of diarrhea, the major consequences of diarrheal diseases, resulting from excessive chloride transport are common to all, and include dehydration, acidosis, impaired growth and death.

Acute and chronic diarrheas represent a major medical problem in many areas of the world. Diarrhea is both a significant factor in malnutrition and the leading cause of death (5,000,000 deaths/year) in children less than five years old.

Secretory diarrheas are also a dangerous condition in patients of acquired immunodeficiency syndrome (AIDS) and chronic inflammatory bowel disease (IBD). 16 million travelers to developing countries from industrialized nations every year develop diarrhea, with the severity and number of cases of diarrhea varying depending on the country and area of travel.

Diarrhea in barn animals and pets such as cows, pigs and horses, sheep, goats, cats and dogs, also known as scours, is a major cause of death in these animals. Diarrhea can result from any major transition, such as weaning or physical movement, as well as in response to a variety of bacterial or viral infections and generally occurs within the first few hours of the animal's life.

The most common diarrheal causing bacteria is enterotoxogenic *E. coli* (ETEC) having the K99 pilus antigen. Common viral causes of diarrhea include rotavirus and coronavirus. Other infectious agents include cryptosporidium, *giardia lamblia*, and *salmonella*, among others.

Symptoms of rotaviral infection include excretion of watery feces, dehydration and weakness. Coronavirus causes a more severe illness in the newborn animals, and has a higher mortality rate than rotaviral infection. Often, however, a young animal may be infected with more than one virus or with a combination of viral and bacterial microorganisms at one time. This dramatically increases the severity of the disease.

Accordingly, there is a need for modulators of CFTR activity, and compositions thereof that can be used to modulate the activity of the CFTR in the cell membrane of a mammal.

There is a need for methods of treating CFTR mediated diseases using such modulators of CFTR activity.

There is a need for methods of modulating CFTR activity in an ex vivo cell membrane of a mammal.

SUMMARY OF THE INVENTION

It has now been found that compounds of this invention, and pharmaceutically acceptable compositions thereof, are useful as modulators of ABC transporter activity. These compounds have the general formula I:

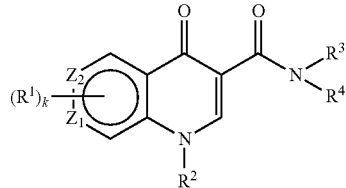

or a pharmaceutically acceptable salt thereof, wherein $R^1$, $R^2$, $R^3$, $R^4$, $Z_1$, $Z_2$, and k are described generally and in classes and subclasses below.

These compounds and pharmaceutically acceptable compositions are useful for treating or lessening the severity of a variety of diseases, disorders, or conditions, including, but not limited to, cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders asuch as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, Straussler-Scheinker syndrome, COPD, dry-eye disease, and Sjogren's disease.

DETAILED DESCRIPTION OF THE INVENTION

I. General Description of Compounds of the Invention:

The present invention relates to compounds of formula I useful as modulators of ABC transporter activity:

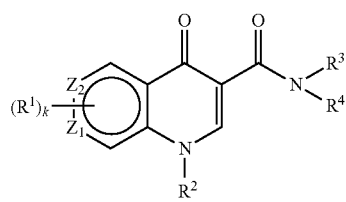

or a pharmaceutically acceptable salt thereof.

$R^3$ is $-Z^A R^5$, wherein each $Z^A$ is independently a bond or an unsubstituted $C_{1-6}$ branched or straight aliphatic chain, and $R^5$ is an aryl or a heteroaryl, either of which is optionally substituted, or $R^5$ is a 3-6 membered cycloaliphatic substituted with 1-2 groups independently selected from optionally substituted aryl and optionally substituted heteroaryl.

Each $R^1$ is independently $-X-R^A$, wherein each X is independently a bond or an optionally substituted $C_{1-6}$ straight or branched aliphatic chain wherein up to two carbon units of X are optionally and independently replaced by —CO—, —CS—, —COCO—, —CONR'—, —CONR'NR'—, —CO$_2$—, —COO—, —NR'CO$_2$—, —O—, —NR'CONR'—, —OCONR'—, —NR'NR', —NR'NR'CO—, —NR'CO—, —S—, —SO, —SO$_2$—, —NR'—, —SO$_2$NR'—, —NR'SO$_2$—, or —NR'SO$_2$NR'—; and $R^A$ is independently R', halo, —NO$_2$, —CN, —CF$_3$, or —OCF$_3$. R' is hydrogen or an optionally substituted group selected from a $C_{1-8}$ aliphatic, a 3-8 membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

$R^2$ is hydrogen.

$R^4$ is hydrogen or a $C_{1-6}$ aliphatic group optionally substituted with $-X-R^A$.

Each of $Z_1$ or $Z_2$ is independently —CH—, —CR'—, or N, and at least one of $Z_1$ or $Z_2$ is N.

2. Compounds and Definitions:

Compounds of this invention include those described generally above, and are further illustrated by the classes, subclasses, and species disclosed herein. As used herein, the following definitions shall apply unless otherwise indicated.

The term "ABC-transporter" as used herein means an ABC-transporter protein or a fragment thereof comprising at least one binding domain, wherein said protein or fragment thereof is present in vivo or in vitro. The term "binding domain" as used herein means a domain on the ABC-transporter that can bind to a modulator. See, e.g., Hwang, T. C. et al., J. Gen. Physiol. (1998): 111(3), 477-90.

The term "CFTR" as used herein means cystic fibrosis transmembrane conductance regulator or a mutation thereof capable of regulator activity, including, but not limited to, ΔF508 CFTR and G551D CFTR (see, e.g., http://www.genet.sickkids.on.ca/cftr/, for CFTR mutations).

The term "modulating" as used herein means increasing or decreasing by a measurable amount.

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausolito: 1999, and "March's Advanced Organic Chemistry", 5th Ed., Ed.: Smith, M. B. and March, J., John Wiley & Sons, N.Y.: 2001, the entire contents of which are hereby incorporated by reference.

As described herein, compounds of the invention may optionally be substituted with one or more substituents, such as are illustrated generally above, or as exemplified by particular classes, subclasses, and species of the invention.

As used herein the term "aliphatic" encompasses the terms alkyl, alkenyl, alkynyl, each of which being optionally substituted as set forth below.

As used herein, an "alkyl" group refers to a saturated aliphatic hydrocarbon group containing 1-12 (e.g., 1-8, 1-6, or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, or heterocycloaliphaticamino], sulfonyl [e.g., aliphatic-SO$_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, aralkyl, (alkoxyaryl)alkyl, (sulfonylamino)alkyl (such as (alkyl-SO$_2$-amino)alkyl), aminoalkyl, amidoalkyl, (cycloaliphatic)alkyl, or haloalkyl.

As used herein, an "alkenyl" group refers to an aliphatic carbon group that contains 2-8 (e.g., 2-12, 2-6, or 2-4) carbon atoms and at least one double bond. Like an alkyl group, an alkenyl group can be straight or branched. Examples of an alkenyl group include, but are not limited to allyl, isoprenyl, 2-butenyl, and 2-hexenyl. An alkenyl group can be optionally substituted with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, heterocycloaliphaticamino, or aliphaticsulfonylamino], sulfonyl [e.g., alkyl-SO$_2$—, cycloaliphatic-SO$_2$—, or aryl-SO$_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-SO$_2$-amino)alkenyl), aminoalkenyl, amidoalkenyl, (cycloaliphatic)alkenyl, or haloalkenyl.

As used herein, an "alkynyl" group refers to an aliphatic carbon group that contains 2-8 (e.g., 2-12, 2-6, or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl [e.g., aliphaticsulfanyl or cycloaliphaticsulfanyl], sulfinyl [e.g., aliphaticsulfinyl or cycloaliphaticsulfinyl], sulfonyl [e.g., aliphatic-SO$_2$—, aliphaticamino-SO$_2$—, or cycloaliphatic-SO$_2$—], amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl], urea, thiourea, sulfamoyl, sulfamide, alkoxycarbonyl, alkylcarbonyloxy, cycloaliphatic, heterocycloaliphatic, aryl, heteroaryl, acyl [e.g., (cycloaliphatic)carbonyl or (heterocycloaliphatic)carbonyl], amino [e.g., aliphaticamino], sulfoxy, oxo, carboxy, carbamoyl, (cycloaliphatic)oxy, (heterocycloaliphatic)oxy, or (heteroaryl)alkoxy.

As used herein, an "amido" encompasses both "aminocarbonyl" and "carbonylamino". These terms when used alone or in connection with another group refer to an amido group such as —N(R$^X$)—C(O)—R$^Y$ or —C(O)—N(R$^X$)$_2$, when used terminally, and —C(O)—N(R$^X$)— or —N(R$^X$)—C(O)—when used internally, wherein R$^X$ and R$^Y$ are defined below. Examples of amido groups include alkylamido (such as alkylcarbonylamino or alkylaminocarbonyl), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido.

As used herein, an "amino" group refers to —NR$^X$R$^Y$ wherein each of R$^X$ and R$^Y$ is independently hydrogen, aliphatic, cycloaliphatic, (cycloaliphatic)aliphatic, aryl, araliphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic) aliphatic)carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic) carbonyl, each of which being defined herein and being optionally substituted. Examples of amino groups include alkylamino, dialkylamino, or arylamino. When the term "amino" is not the terminal group (e.g., alkylcarbonylamino), it is represented by —$NR^X$—. $R^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzofused 2-3 membered carbocyclic rings. For example, a benzofused group includes phenyl fused with two or more $C_{4-8}$ carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic ring of a benzofused bicyclic or tricyclic aryl); nitro; carboxy; amido; acyl [e.g., (aliphatic)carbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphatic-$SO_2$— or amino-$SO_2$—]; sulfinyl [e.g., aliphatic-S(O)— or cycloaliphatic-S(O)—]; sulfanyl [e.g., aliphatic-S—]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di (such as p,m-dihaloaryl), and (trihalo)aryl]; (carboxy)aryl [e.g., (alkoxycarbonyl)aryl, ((aralkyl)carbonyloxy)aryl, and (alkoxycarbonyl)aryl]; (amido)aryl [e.g., (aminocarbonyl)aryl, (((alkylamino)alkyl)aminocarbonyl)aryl, (alkylcarbonyl)aminoaryl, (arylaminocarbonyl)aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (aminosulfonyl)aryl]; (alkylsulfonyl)aryl; (cyano)aryl; (hydroxyalkyl)aryl; ((alkoxy)alkyl)aryl; (hydroxy)aryl, ((carboxy)alkyl)aryl; (((dialkyl)amino)alkyl)aryl; (nitroalkyl)aryl; (((alkylsulfonyl)amino)alkyl)aryl; ((heterocycloaliphatic)carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "araliphatic" such as an "aralkyl" group refers to an aliphatic group (e.g., a $C_{1-4}$ alkyl group) that is substituted with an aryl group. "Aliphatic," "alkyl," and "aryl" are defined herein. An example of an araliphatic such as an aralkyl group is benzyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl], cycloaliphatic [e.g., cycloalkyl or cycloalkenyl], (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino], cyano, halo, hydroxy, acyl, mercapto, alkylsulfanyl, sulfoxy, urea, thiourea, sulfamoyl, sulfamide, oxo, or carbamoyl.

As used herein, a "bicyclic ring system" includes 8-12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "carbocycle" or "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2]octyl, bicyclo[3.3.1]nonyl, bicyclo[3.3.2.]decyl, bicyclo[2.2.2]octyl, adamantyl, or ((aminocarbonyl)cycloalkyl)cycloalkyl.

A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, cyclopentenyl, bicyclo[2.2.2]octenyl, or bicyclo[3.3.1]nonenyl.

A cycloalkyl or cycloalkenyl group can be optionally substituted with one or more substituents such as phosphor, aliphatic [e.g., alkyl, alkenyl, or alkynyl], cycloaliphatic, (cycloaliphatic) aliphatic, heterocycloaliphatic, (heterocycloaliphatic) aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic)aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl], cyano, halo, hydroxy, mercapto, sulfonyl [e.g., alkyl-$SO_2$— and aryl-$SO_2$—], sulfinyl [e.g., alkyl-S(O)—], sulfanyl [e.g., alkyl-S—], sulfoxy, urea, thiourea, sulfamoyl, sulfamide, oxo, or carbamoyl.

As used herein, the term "heterocycle" or "heterocycloaliphatic" encompasses a heterocycloalkyl group and a heterocycloalkenyl group, each of which being optionally substituted as set forth below.

As used herein, a "heterocycloalkyl" group refers to a 3-10 membered mono- or bicylic (fused or bridged) (e.g., 5- to 10-membered mono- or bicyclic) saturated ring structure, in which one or more of the ring atoms is a heteroatom (e.g., N, O, S, or combinations thereof).

Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.0$^{3,7}$]nonyl. A monocyclic heterocycloalkyl group can be fused with a phenyl moiety to form structures, such as tetrahydroisoquinoline, which would be categorized as heteroaryls.

A "heterocycloalkenyl" group, as used herein, refers to a mono- or bicylic (e.g., 5- to 10-membered mono- or bicyclic) non-aromatic ring structure having one or more double bonds, and wherein one or more of the ring atoms is a heteroatom (e.g., N, O, or S). Monocyclic and bicyclic heterocycloaliphatics are numbered according to standard chemical nomenclature.

A heterocycloalkyl or heterocycloalkenyl group can be optionally substituted with one or more substituents such as phosphor, aliphatic [e.g., alkyl, alkenyl, or alkynyl], cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic) aliphatic)carbonylamino, (aryl)carbonylamino, (araliphatic)carbonylamino, (heterocycloaliphatic)carbonylamino, ((heterocycloaliphatic) aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic) carbonyl, or (heteroaraliphatic)carbonyl], nitro, cyano, halo, hydroxy, mercapto, sulfonyl [e.g., alkylsulfonyl or arylsulfonyl], sulfinyl [e.g., alkylsulfinyl], sulfanyl [e.g., alkylsulfanyl], sulfoxy, urea, thiourea, sulfamoyl, sulfamide, oxo, or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl,cinnolyl, phthalazyl, quinazolyl, quinoxalyl, isoquinolyl, 4H-quinolizyl, benzo-1,2,5-thiadiazolyl, or 1,8-naphthyridyl.

Without limitation, monocyclic heteroaryls include furyl, thiophenyl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizinyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic or heterocyclic ring of a bicyclic or tricyclic heteroaryl); carboxy; amido; acyl [e.g., aliphaticcarbonyl; (cycloaliphatic)carbonyl; ((cycloaliphatic)aliphatic) carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphaticsulfonyl or amino sulfonyl]; sulfinyl [e.g., aliphaticsulfinyl]; sulfanyl [e.g., aliphaticsulfanyl]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono- and di-(halo)heteroaryl]; (carboxy)heteroaryl [e.g., (alkoxycarbonyl)heteroaryl]; cyanoheteroaryl; aminoheteroaryl [e.g., ((alkylsulfonyl)amino)heteroaryl and ((dialkyl)amino)heteroaryl]; (amido)heteroaryl [e.g., aminocarbonylheteroaryl, ((alkylcarbonyl)amino)heteroaryl, ((((alkyl)amino)alkyl)aminocarbonyl)heteroaryl, (((heteroaryl)amino)carbonyl)heteroaryl, ((heterocycloaliphatic)carbonyl)heteroaryl, and ((alkylcarbonyl)amino)heteroaryl]; (cyanoalkyl)heteroaryl; (alkoxy)heteroaryl; (sulfamoyl)heteroaryl [e.g., (aminosulfonyl)heteroaryl]; (sulfonyl)heteroaryl [e.g., (alkylsulfonyl)heteroaryl]; (hydroxyalkyl)heteroaryl; (alkoxyalkyl)heteroaryl; (hydroxy)heteroaryl; ((carboxy)alkyl)heteroaryl; (((dialkyl)amino)alkyl]heteroaryl; (heterocycloaliphatic)heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl)heteroaryl [e.g., (alkylcarbonyl)heteroaryl]; (alkyl)heteroaryl, and (haloalkyl)heteroaryl [e.g., trihaloalkylheteroaryl].

A "heteroaraliphatic" (such as a heteroaralkyl group) as used herein, refers to an aliphatic group (e.g., a $C_{1-4}$ alkyl group) that is substituted with a heteroaryl group. "Aliphatic," "alkyl," and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, "cyclic moiety" and "cyclic group" refer to mono-, bi-, and tri-cyclic ring systems including cycloaliphatic, heterocycloaliphatic, aryl, or heteroaryl, each of which has been previously defined.

As used herein, a "bridged bicyclic ring system" refers to a bicyclic heterocyclicaliphatic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxabicyclo[2.2.2]octyl, 1-azabicyclo[2.2.2]octyl, 3-azabicyclo[3.2.1]octyl, and 2,6-dioxa-tricyclo[3.3.1.0$^{3,7}$] nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "acyl" group refers to a formyl group or $R^X$—C(O)— (such as alkyl-C(O)—, also referred to as "alkylcarbonyl") where $R^X$ and "alkyl" have been defined previously. Acetyl and pivaloyl are examples of acyl groups.

As used herein, an "aroyl" or "heteroaroyl" refers to an aryl-C(O)— or a heteroaryl-C(O)—. The aryl and heteroaryl portion of the aroyl or heteroaroyl is optionally substituted as previously defined.

As used herein, an "alkoxy" group refers to an alkyl-O— group where "alkyl" has been defined previously.

As used herein, a "carbamoyl" group refers to a group having the structure —O—CO—NR$^X$R$^Y$ or —NR$^X$—CO—O—R$^Z$, wherein R$^X$ and R$^Y$ have been defined above and R$^Z$ can be aliphatic, aryl, aralphatic, heterocycloaliphatic, heteroaryl, or heteroaraliphatic.

As used herein, a "carboxy" group refers to —COOH, —COOR$^X$, —OC(O)H, —OC(O)R$^X$, when used as a terminal group; or —OC(O)— or —C(O)O— when used as an internal group.

As used herein, a "haloaliphatic" group refers to an aliphatic group substituted with 1-3 halogen. For instance, the term haloalkyl includes the group —CF$_3$.

As used herein, a "mercapto" group refers to —SH.

As used herein, a "sulfo" group refers to —SO$_3$H or —SO$_3$R$^X$ when used terminally or —S(O)$_3$— when used internally.

As used herein, a "sulfamide" group refers to the structure —NR$^X$—S(O)$_2$—NR$^Y$R$^Z$ when used terminally and —NR$^X$—S(O)$_2$—NR$^Y$— when used internally, wherein R$^X$, R$^Y$, and R$^Z$ have been defined above.

As used herein, a "sulfonamide" group refers to the structure —S(O)$_2$—NR$^X$R$^Y$ or —NR$^X$—S(O)$_2$—R$^Z$ when used terminally; or —S(O)$_2$—NR$^X$— or —NR$^X$—S(O)$_2$— when used internally, wherein R$^X$, R$^Y$, and R$^Z$ are defined above.

As used herein a "sulfanyl" group refers to —S—R$^X$ when used terminally and —S— when used internally, wherein R$^X$ has been defined above. Examples of sulfanyls include aliphatic-S—, cycloaliphatic-S—, aryl-S—, or the like.

As used herein a "sulfinyl" group refers to —S(O)—R$^X$ when used terminally and —S(O)—when used internally, wherein R$^X$ has been defined above. Exemplary sulfinyl groups include aliphatic-S(O)—, aryl-S(O)—, (cycloaliphatic(aliphatic))-S(O)—, cycloalkyl-S(O)—, heterocycloaliphatic-S(O)—, heteroaryl-S(O)—, or the like.

As used herein, a "sulfonyl" group refers to —S(O)$_2$—R$^X$ when used terminally and —S(O)$_2$— when used internally, wherein R$^X$ has been defined above. Exemplary sulfonyl groups include aliphatic-S(O)$_2$—, aryl-S(O)$_2$—, (cycloaliphatic(aliphatic))-S(O)$_2$—, cycloaliphatic-S(O)$_2$—, heterocycloaliphatic-S(O)$_2$—, heteroaryl-S(O)$_2$—, (cycloaliphatic(amido(aliphatic)))-S(O)$_2$— or the like.

As used herein, a "sulfoxy" group refers to –O—SO—R$^X$ or —SO—O—R$^X$, when used terminally and —O—S(O)— or —S(O)—O— when used internally, where R$^X$ has been defined above.

As used herein, a "halogen" or "halo" group refers to fluorine, chlorine, bromine or iodine.

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refer to —C(O)—.

As used herein, an "oxo" refers to =O.

As used herein, the term "phospho" refers to phosphinates and phosphonates. Examples of phosphinates and phosphonates include —P(O)(R$^P$)$_2$, wherein R$^P$ is aliphatic, alkoxy, aryloxy, heteroaryloxy, (cycloaliphatic)oxy, (heterocycloaliphatic)oxy aryl, heteroaryl, cycloaliphatic or amino.

As used herein, an "aminoalkyl" refers to the structure (R$^X$)$_2$N-alkyl-.

As used herein, a "cyanoalkyl" refers to the structure (NC)-alkyl-.

As used herein, a "urea" group refers to the structure —NR$^X$—CO—NR$^Y$R$^Z$ and a "thiourea" group refers to the structure —NR$^X$—CS—NR$^Y$R$^Z$ when used terminally and —NR$^X$—CO—NR$^Y$— or —NR$^X$—CS—NR$^Y$— when used internally, wherein R$^X$, R$^Y$, and R$^Z$ have been defined above.

As used herein, a "guanidine" group refers to the structure —N=C(N(R$^X$R$^Y$))N(R$^X$R$^Y$) or —NR$^X$—C(=NR$^X$)NR$^X$R$^Y$ wherein R$^X$ and R$^Y$ have been defined above.

As used herein, the term "amidino" group refers to the structure —C=(NR$^X$)N(R$^X$R$^Y$) wherein R$^X$ and R$^Y$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., R$^X$O(O)C-alkyl is an example of a carboxy group used terminally. A group is internal when the group is present in the middle of a substituent of the chemical structure. Alkylcarboxy (e.g., alkyl-C(O)O— or alkyl-OC(O)—) and alkylcarboxyaryl (e.g., alkyl-C(O)O-aryl- or alkyl-O(CO)-aryl-) are examples of carboxy groups used internally.

As used herein, an "aliphatic chain" refers to a branched or straight aliphatic group (e.g., alkyl groups, alkenyl groups, or alkynyl groups). A straight aliphatic chain has the structure —[CH$_2$]$_v$—, where v is 1-12. A branched aliphatic chain is a straight aliphatic chain that is substituted with one or more aliphatic groups. A branched aliphatic chain has the structure —[CQQ]$_v$- where each Q is independently a hydrogen or an aliphatic group; however, at least one Q shall be an aliphatic group in at least one instance. The term aliphatic chain includes alkyl chains, alkenyl chains, and alkynyl chains, where alkyl, alkenyl, and alkynyl are defined above.

The phrase "optionally substituted" is used interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables $R^1$, $R^2$, $R^3$, and $R^4$, and other variables contained in formulae described herein encompass specific groups, such as alkyl and aryl. Unless otherwise noted, each of the specific groups for the variables $R^1$, $R^2$, $R^3$, and $R^4$, and other variables contained therein can be optionally substituted with one or more substituents described herein. Each substituent of a specific group is further optionally substituted with one to three of halo, cyano, oxo, alkoxy, hydroxy, amino, nitro, aryl, cycloaliphatic, heterocycloaliphatic, heteroaryl, haloalkyl, and alkyl. For instance, an alkyl group can be substituted with alkylsulfanyl and the alkylsulfanyl can be optionally substituted with one to three of halo, cyano, oxo, alkoxy, hydroxy, amino, nitro, aryl, haloalkyl, and alkyl. As an additional example, the cycloalkyl portion of a (cycloalkyl)carbonylamino can be optionally substituted with one to three of halo, cyano, alkoxy, hydroxy, nitro, haloalkyl, and alkyl. When two alkoxy groups are bound to the same atom or adjacent atoms, the two alkxoy groups can form a ring together with the atom(s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an "effective amount" is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., Cancer Chemother. Rep., 50: 219 (1966). Body surface area may be approximately determined from height and weight of the patient. See, e.g., Scientific Tables, Geigy Pharmaceuticals, Ardsley, New York, 537 (1970). As used herein, "patient" refers to a mammal, including a human.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays, or as therapeutic agents. For example, when $R^2$ in compounds of formula I is hydrogen, compounds of formula I may exist as tautomers:

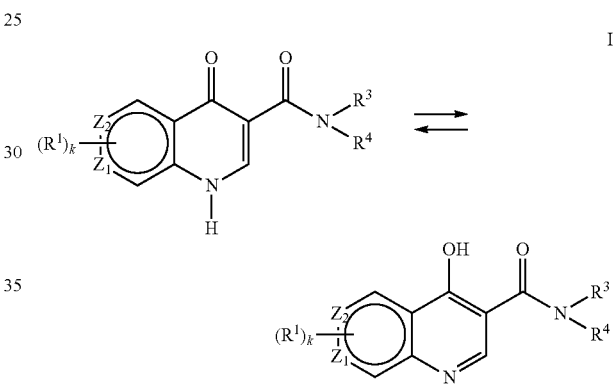

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

3. Description of Exemplary Compounds:

In some embodiments of the present invention, $R^3$ is selected from:

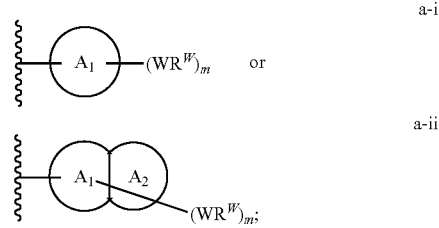

wherein ring $A_1$ is a 5-6 membered aromatic monocyclic ring having 0-4 heteroatoms independently selected from nitrogen, oxygen, or sulfur; ring $A_1$ is a 3-6 membered cycloaliphatic substituted with 1-2 groups independently selected from optionally substituted aryl and optionally substituted heteroaryl; or $A_1$ and $A_2$, together, form an 8-14 membered bicyclic aryl or tricyclic aryl; or $A_1$ and $A_2$, together, form an 8-14 membered bicyclic heteroaryl or tricyclic heteroaryl having 1-4 heteroatoms independently selected from nitrogen, oxygen, or sulfur. Each W is a bond or an optionally substituted $C_{1-6}$ straight or branched aliphatic chain wherein up to 2 of the carbon units are optionally and independently replaced by —CO—, —CS—, —COCO—, —CONR'—, —CONR'NR'—, —CO$_2$—, —COO—, —NR'CO$_2$—, —O—, —NR'CONR'—, —OCONR'—, —NR'NR'—, —NR'NR'CO—, —NR'CO—, —S—, —SO, —SO$_2$—, —NR'—, —SO$_2$NR'—, —NR'SO$_2$—, or —NR'SO$_2$NR'—; and $R^W$ is independently R', halo, —NO$_2$, —CN, —CF$_3$, or —OCF$_3$; m is 0-5; and R' is defined above.

In some embodiments, $A_1$ is an optionally substituted 6 membered aromatic ring having 0-4 heteroatoms, wherein said heteroatom is nitrogen. In some embodiments, $A_1$ is an optionally substituted phenyl. Or, $A_1$ is an optionally substituted pyridyl, pyrimidinyl, pyrazinyl or triazinyl. Or, $A_1$ is an optionally substituted pyrazinyl or triazinyl. Or, $A_1$ is an optionally substituted pyridyl.

In some embodiments, $A_1$ is an optionally substituted 5-membered aromatic ring having 1-3 heteroatoms, wherein said heteroatom is independently selected from nitrogen, oxygen, and sulfur. In some embodiments, $A_1$ is an optionally substituted 5-membered aromatic ring having 1-2 nitrogen atoms. In one embodiment, $A_1$ is an optionally substituted 5-membered aromatic ring other than thiazolyl.

In some embodiments, $A_2$ is an optionally substituted 6 membered aromatic ring having 0-4 heteroatoms, wherein said heteroatom is nitrogen. In some embodiments, $A_2$ is an optionally substituted phenyl. Or, $A_2$ is an optionally substituted pyridyl, pyrimidinyl, pyrazinyl, or triazinyl.

In some embodiments, $A_2$ is an optionally substituted 5-membered aromatic ring having 0-3 heteroatoms, wherein said heteroatom is independently selected from nitrogen, oxygen, and sulfur. In some embodiments, $A_2$ is an optionally substituted 5-membered aromatic ring having 1-2 nitrogen atoms. In certain embodiments, $A_2$ is an optionally substituted pyrrolyl.

In some embodiments, $A_2$ is an optionally substituted 5-7 membered saturated or unsaturated heterocyclic ring having 1-3 heteroatoms independently selected from nitrogen, sulfur, or oxygen. Exemplary such rings include piperidyl, piperazyl, morpholinyl, thiomorpholinyl, pyrrolidinyl, tetrahydrofuranyl, etc.

In some embodiments, $A_2$ is an optionally substituted 5-10 membered saturated or unsaturated carbocyclic ring. In one embodiment, $A_2$ is an optionally substituted 5-10 membered saturated carbocyclic ring. Exemplary such rings include cyclohexyl, cyclopentyl, etc.

In some embodiments, ring $A_2$ is selected from:

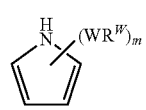

i

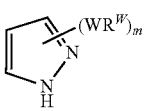

ii

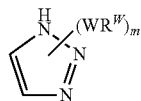

iii

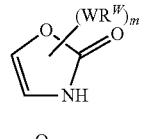

iv

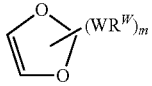

v

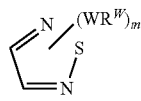

vi

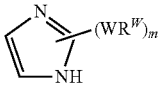

vii

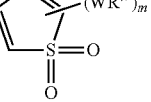

viii

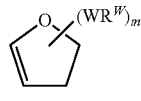

ix

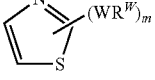

x

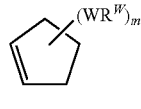

xi

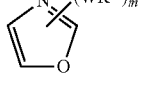

xii

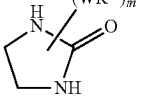

xiii

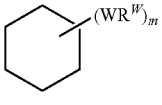

xiv

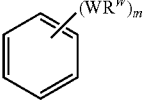

xv

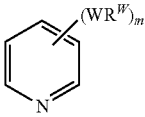

xvi

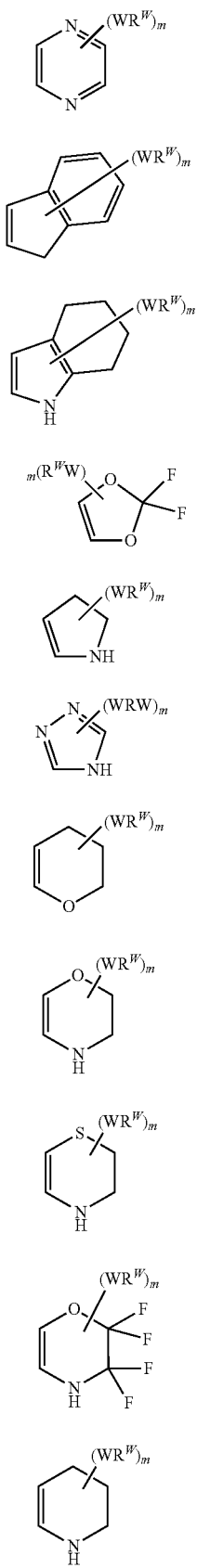
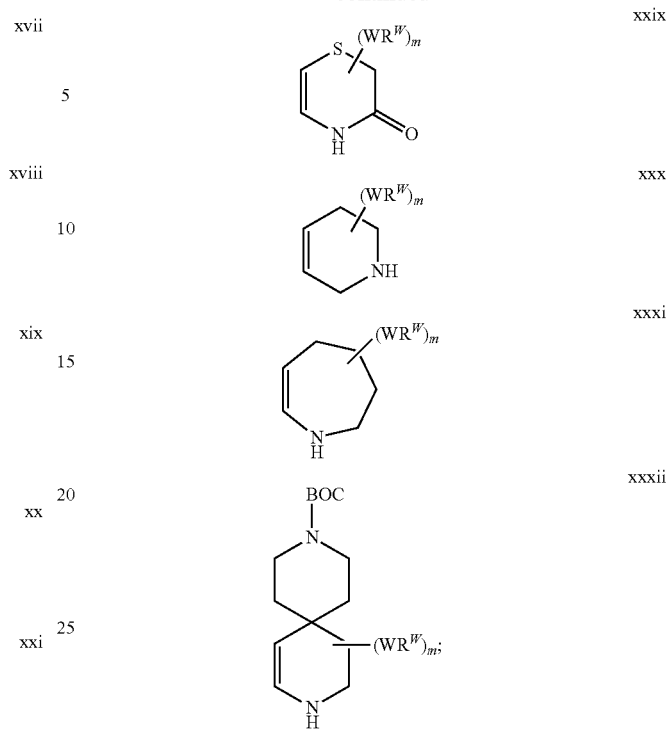

wherein ring $A_2$ is fused to ring $A_1$ through two adjacent ring atoms.

In other embodiments, W is a bond or is an optionally substituted $C_{1-6}$ straight or branched aliphatic chain wherein one or two carbon units are optionally and independently replaced by —O—, —NR'—, —S—, —SO—, —SO$_2$—, or —COO—, —CO—, —SO$_2$NR'—, —NR'SO$_2$—, —C(O)NR'—, —NR'C(O)—, —OC(O)—, —OC(O)NR'—, and $R^W$ is R' or halo. In still other embodiments, each occurrence of —WR$^W$ is independently —C$_{1-3}$ alkyl, —C$_{1-3}$ perhaloalkyl, —O(C$_{1-3}$ alkyl), —CF$_3$, —OCF$_3$, —SCF$_3$, —F, —Cl, —Br, or —COOR', —COR', —O(CH$_2$)$_2$N(R')(R'), —O(CH$_2$)N(R')(R'), —CON(R')(R'), —(CH$_2$)$_2$OR', —(CH$_2$)OR', optionally substituted 5-7 membered heterocylic ring, optionally substituted monocyclic or bicyclic aromatic ring, optionally substituted arylsulfone, optionally substituted 5-membered heteroaryl ring, —N(R')(R'), —(CH$_2$)$_2$N(R')(R'), or —(CH$_2$)N(R')(R').

In one embodiment of Ar$_1$ in formula a-i, ring A$_1$ is a phenyl ring, m is 1, and WR$^W$ is independently optionally substituted pyrrolidine or piperidine.

In some embodiments, m is 0. Or, m is 1. Or, m is 2. In some embodiments, m is 3. In yet other embodiments, m is 4.

In one embodiment of the present invention, $R^1$, $R^2$, $R^3$, and $R^4$ are simultaneously hydrogen.

In another embodiment of the present invention, k is 1 or 2 and each $R^1$ is independently $C_{1-3}$ alkyl or $C_{3-6}$ cycloalkyl.

In one embodiment, k is 1 or 2, and each $R^1$ is halo.

In some embodiments, X is a bond or is an optionally substituted $C_{1-6}$ branched or straight aliphatic chain wherein one or two non-adjacent carbon units are optionally and independently replaced by —O—, —NR'—, —S—, —SO$_2$—, or —COO—, —CO—, and $R^X$ is R' or halo. In still other embodiments, each occurrence of —XR$^X$ is independently —C$_{1-3}$ alkyl, —O(C$_{1-3}$ alkyl), —CF$_3$, —OCF$_3$, —SCF$_3$, —F, —Cl, —Br, OH, —COOR', —COR', —O(CH$_2$)$_2$N(R')(R'), —O(CH$_2$)N(R')(R'), —CON(R')(R'), —(CH$_2$)$_2$OR', —(CH$_2$)OR', optionally substituted phenyl, —N(R')(R'), —(CH$_2$)$_2$N(R')(R'), or —(CH$_2$)N(R')(R').

In one embodiment, R$^1$ is H, —C$_{1-4}$ aliphatic, halo, or —C$_{3-6}$ cycloaliphatic.

In some embodiments, R$^1$ is H, or C$_1$-C$_3$ alkyl. For instance, R$^1$ is H or —CH$_3$.

In some embodiments, R$^4$ is hydrogen. In certain other embodiment, R$^4$ is C$_{1-4}$ straight or branched aliphatic.

In some embodiments, R$^W$ is selected from halo, cyano, —CF$_3$, —CHF$_2$, —OCHF$_2$, Me, Et, —CH(Me)$_2$, —CHMeEt, n-propyl, t-butyl, —OMe, —OEt, —OPh, O-fluorophenyl, —O-difluorophenyl, —O-methoxyphenyl, —O-tolyl, —O-benzyl, —SMe, —SCF$_3$, —SCHF$_2$, —SEt, —CH$_2$CN, —NH$_2$, —NHMe, —N(Me)$_2$, —NHEt, —N(Et)$_2$, —C(O)CH$_3$, —C(O)Ph, —C(O)NH$_2$, —SPh, —SO$_2$— (amino-pyridyl), —SO$_2$NH$_2$, —SO$_2$Ph, —SO$_2$NHPh, —SO$_2$—N-morpholino, —SO$_2$—N-pyrrolidyl, N-pyrrolyl, N-morpholino, 1-piperidyl, phenyl, benzyl, (cyclohexyl-methylamino)methyl, 4-Methyl-2,4-dihydro-pyrazol-3-one-2-yl, benzimidazol-2y1, furan-2-yl, 4-methyl-4H-[1,2,4]triazol-3-yl, 3-(4'-chlorophenyl)-[1,2,4]oxadiazol-5-yl, —NHC(O)Me, NHC(O)Et, —NHC(O)Ph, —NHSO$_2$Me, 2-indolyl, 5-indolyl, —CH$_2$CH$_2$OH, —OCF$_3$, O-(2,3-dimethylphenyl), 5-methylfuryl, —SO$_2$—N-piperidyl, 2-tolyl, 3-tolyl, 4-tolyl, O-butyl, NHCO$_2$C(Me)$_3$, CO$_2$C(Me)$_3$, isopropenyl, n-butyl, —O-(2,4-dichlorophenyl), NHSO$_2$PhMe, O-(3-chloro-5-trifluoromethyl-2-pyridyl), phenylhydroxymethyl, 2,5-dimethylpyrrolyl, NHCOCH$_2$C(Me)$_3$, O-(2-tert-butyl)phenyl, 2,3-dimethylphenyl, 3,4-dimethylphenyl, 4-hydroxymethyl phenyl, 4-dimethylaminophenyl, 2-trifluoromethylphenyl, 3-trifluoromethylphenyl, 4-trifluoromethylphenyl, 4-cyanomethylphenyl, 4-isobutylphenyl, 3-pyridyl, 4-pyridyl, 4-isopropylphenyl, 3-isopropylphenyl, 2-methoxyphenyl, 3-methoxyphenyl, 4-methoxyphenyl, 3,4-methylenedioxyphenyl, 2-ethoxyphenyl, 3-ethoxyphenyl, 4-ethoxyphenyl, 2-methylthiophenyl, 4-methylthiophenyl, 2,4-dimethoxyphenyl, 2,5-dimethoxyphenyl, 2,6-dimethoxyphenyl, 3,4-dimethoxyphenyl, 5-chloro-2-methoxyphenyl, 2-OCF$_3$-phenyl, 3-trifluoromethoxy-phenyl, 4-trifluoromethoxyphenyl, 2-phenoxyphenyl, 4-phenoxyphenyl, 2-fluoro-3-methoxyphenyl, 2,4-dimethoxy-5-pyrimidyl, 5-isopropyl-2-methoxyphenyl, 2-fluorophenyl, 3-fluorophenyl, 4-fluorophenyl, 3-cyanophenyl, 3-chlorophenyl, 4-chlorophenyl, 2,3-difluorophenyl, 2,4-difluorophenyl, 2,5-difluorophenyl, 3,4-difluorophenyl, 3,5-difluorophenyl, 3-chloro-4-fluoro-phenyl, 3,5-dichlorophenyl, 2,5-dichlorophenyl, 2,3-dichlorophenyl, 3,4-dichlorophenyl, 2,4-dichlorophenyl, 3-methoxycarbonylphenyl, 4-methoxycarbonyl phenyl, 3-isopropyloxycarbonylphenyl, 3-acetamidophenyl, 4-fluoro-3-methylphenyl, 4-methanesulfinyl-phenyl, 4-methanesulfonyl-phenyl, 4-N-(2-N,N-dimethylaminoethyl)carbamoylphenyl, 5-acetyl-2-thienyl, 2-benzothienyl, 3-benzothienyl, furan-3-yl, 4-methyl-2-thienyl, 5-cyano-2-thienyl, N'-phenylcarbonyl-N-piperazinyl, —NHCO$_2$Et, —NHCO$_2$Me, N-pyrrolidinyl, —NHSO$_2$(CH$_2$)$_2$ N-piperidine, —NHSO$_2$(CH$_2$)$_2$ N-morpholine, —NHSO$_2$(CH$_2$)$_2$N(Me)$_2$, —COCH$_2$N(Me) COCH$_2$NHMe, —CO$_2$Et, —O-propyl, —CH$_2$CH$_2$NHCO$_2$C (Me)$_3$, hydroxy, aminomethyl, pentyl, adamantyl, cyclopentyl, ethoxyethyl, —C(Me)$_2$CH$_2$OH, —C(Me)$_2$CO$_2$Et, —CHOHMe, CH$_2$CO$_2$Et, —C(Me)$_2$CH$_2$NHCO$_2$C(Me)$_3$, —O(CH$_2$)$_2$OEt, —O(CH$_2$)$_2$OH, —CO$_2$Me, hydroxymethyl, 1-methyl-1-cyclohexyl, 1-methyl-1-cyclooctyl, 1-methyl-1-cycloheptyl, —C(Et)$_2$C(Me)$_3$, —C(Et)$_3$, —CONHCH$_2$CH(Me)$_2$, 2-aminomethyl-phenyl, ethenyl, 1-piperidinylcarbonyl, ethynyl, cyclohexyl, 4-methylpiperidinyl, —OCO$_2$Me, —C(Me)$_2$CH$_2$NHCO$_2$CH$_2$CH(Me)$_2$, —C(Me)$_2$CH$_2$NHCO$_2$CH$_2$CH$_2$CH$_3$, —C(Me)$_2$CH$_2$NHCO$_2$Et, —C(Me)$_2$CH$_2$NHCO$_2$Me, —C(Me)$_2$CH$_2$NHCO$_2$CH$_2$C(Me)$_3$, —CH$_2$NHCOCF$_3$, —CH$_2$NHCO$_2$C(Me)$_3$, —C(Me)$_2$CH$_2$NHCO$_2$(CH$_2$)$_3$CH$_3$, —C(Me)$_2$CH$_2$NHCO$_2$(CH$_2$)$_2$OMe, —C(OH)(CF$_3$)$_2$, —C(Me)$_2$CH$_2$NHCO$_2$CH$_2$-tetrahydrofurane-3-yl, —C(Me)$_2$CH$_2$—O—(CH$_2$)$_2$OMe, or 3-ethyl-2,6-dioxopiperidin-3-yl.

In one embodiment, R' is hydrogen.

In one embodiment, R' is a C$_{1-8}$ aliphatic group, optionally substituted with up to 3 substituents selected from halo, —CN, —CF$_3$, —CHF$_2$, —OCF$_3$, or —OCHF$_2$, wherein up to two carbon units of said C$_{1-8}$ aliphatic is optionally and independently replaced with —CO—, —CONH(C$_{1-4}$ alkyl)-, —CO$_2$—, —OCO—, —N(C$_{1-4}$ alkyl)CO$_2$—, —O—, —N(C$_{1-4}$ alkyl)CON(C$_{1-4}$ alkyl)-, —OCON(C$_{1-4}$ alkyl)-, —N(C$_{1-4}$ alkyl)CO—, —S—, —N(C$_{1-4}$ alkyl)-, —SO$_2$N(C$_{1-4}$ alkyl)-, —N(C$_{1-4}$ alkyl)SO$_2$—, or —N(C$_{1-4}$ alkyl)SO$_2$N(C$_{1-4}$ alkyl)-.

In one embodiment, R' is a 3-8 membered saturated, partially unsaturated, or fully unsaturated monocyclic ring having 0-3 heteroatoms independently selected from nitrogen, oxygen, or sulfur, wherein R' is optionally substituted with up to 3 substituents selected from halo, —CN, —CF$_3$, —CHF$_2$, —OCF$_3$, —OCHF$_2$, or —C$_{1-6}$ alkyl, wherein up to two carbon units of said C$_{1-6}$ alkyl is independently and optionally replaced with —CO—, —CONH(C$_{1-4}$ alkyl)-, —CO$_2$—, —OCO—, —N(C$_{1-4}$ alkyl)CO$_2$—, —O—, —N(C$_{1-4}$ alkyl)CON(C$_{1-4}$ alkyl)-, —OCON(C$_{1-4}$ alkyl)-, —N(C$_{1-4}$ alkyl)CO—, —S—, —N(C$_{1-4}$ alkyl)-, —SO$_2$N(C$_{1-4}$ alkyl)-, —N(C$_{1-4}$ alkyl)SO$_2$—, or —N(C$_{1-4}$ alkyl)SO$_2$N(C$_{1-4}$ alkyl)-.

In one embodiment, R' is an 8-12 membered saturated, partially unsaturated, or fully unsaturated bicyclic ring system having 0-5 heteroatoms independently selected from nitrogen, oxygen, or sulfur; wherein R' is optionally substituted with up to 3 substituents selected from halo, —CN, —CF$_3$, —CHF$_2$, —OCF$_3$, —OCHF$_2$, or —C$_{1-6}$ alkyl, wherein up to two carbon units of said C$_{1-6}$ alkyl is independently and optionally replaced with —CO—, —CONH(C$_{1-4}$ alkyl)-, —CO$_2$—, —OCO—, —N(C$_{1-4}$ alkyl)CO$_2$—, —O—, —N(C$_{1-4}$ alkyl)CON(C$_{1-4}$ alkyl)-, —OCON(C$_{1-4}$ alkyl)-, —N(C$_{1-4}$ alkyl)CO—, —S—, —N(C$_{1-4}$ alkyl)-, —SO$_2$N(C$_{1-4}$ alkyl)-, —N(C$_{1-4}$ alkyl)SO$_2$—, or —N(C$_{1-4}$ alkyl)SO$_2$N(C$_{1-4}$ alkyl)-.

In one embodiment, two occurrences of R' are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur, wherein R' is optionally substituted with up to 3 substituents selected from halo, —CN, —CF$_3$, —CHF$_2$, —OCF$_3$, —OCHF$_2$, or —C$_{1-6}$ alkyl, wherein up to two carbon units of said —C$_{1-6}$ alkyl is independently and optionally replaced with —CO—, —CONH(C$_{1-4}$ alkyl)-, —CO$_2$—, —COO—, —N(C$_{1-4}$ alkyl)CO$_2$—, —O—, —N(C$_{1-4}$ alkyl)CON(C$_{1-4}$ alkyl)-, —OCON(C$_{1-4}$ alkyl)-, —N(C$_{1-4}$ alkyl)CO—, —S—, —N(C$_{1-4}$ alkyl)-, —SO$_2$N(C$_{1-4}$ alkyl)-, —N(C$_{1-4}$ alkyl)SO$_2$—, or —N(C$_{1-4}$ alkyl)SO$_2$N(C$_{1-4}$ alkyl)-.

According to one embodiment, the present invention provides compounds of formula IIA:

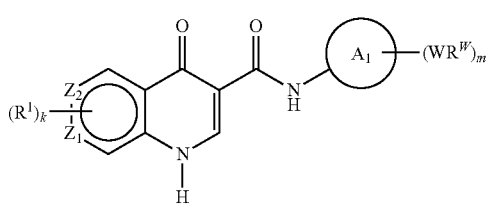

IIA

According to one embodiment, the present invention provides compounds of formula IIB:

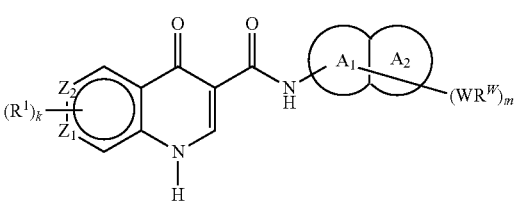

IIB

According to one embodiment, the present invention provides compounds of formula IIIA:

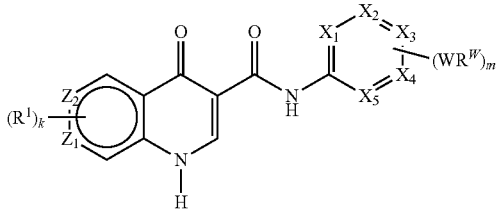

IIIA wherein each of $X_1$, $X_2$, $X_3$, $X_4$, and $X_5$ is independently selected from CH, $CWR^W$, or N.

According to one embodiment, the present invention provides compounds of formula IIIB:

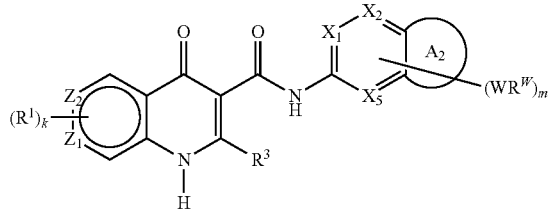

IIIB wherein each of $X_1$, $X_2$, and $X_5$ is independently selected from CH, $CWR^W$, or N.

According to one embodiment, the present invention provides compounds of formula IIIC:

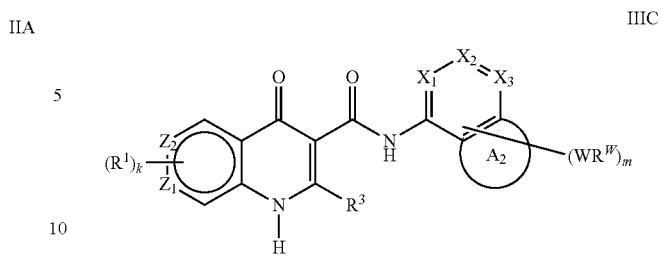

IIIC wherein each of $X_1$, $X_2$, and $X_3$ is independently selected from CH, $CWR^W$, or N.

According to one embodiment, the present invention provides compounds of formula IIID:

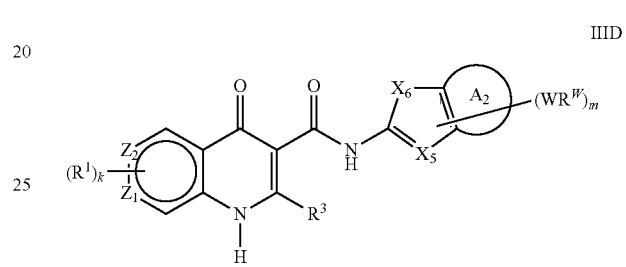

IIID wherein $X_5$ is independently selected from CH, $CWR^W$, or N, and $X_6$ is O, S, or NR'.

According to one embodiment, the present invention provides compounds of formula IIIE:

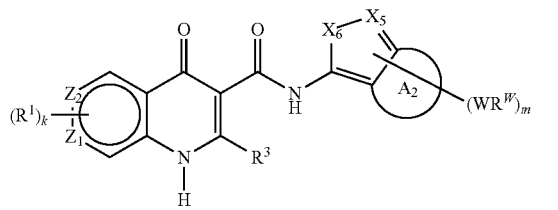

IIIE wherein $X_5$ is independently selected from CH, $CWR^W$, or N, and $X_6$ is O, S, or NR'.

In some embodiments of formula IIIA, each of $X_1$, $X_2$, $X_3$, $X_4$, and $X_5$ is CH.

In some embodiments of formula IIIA, $X_1$, $X_2$, $X_3$, $X_4$, and $X_5$ taken together is an optionally substituted ring selected from pyridyl, pyrazinyl, or pyrimidinyl.

In some embodiments of formula IIIB, formula IIIB', formula IIIC, formula IIIC', formula IIID, formula IIID', formula IIIE, $X_1$, $X_2$, $X_3$, $X_4$, $X_5$, or $X_6$, taken together with ring $A_2$ is an optionally substituted ring selected from:

b-i

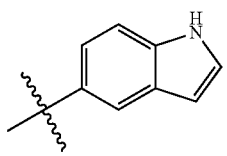

b-ii 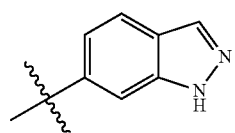
b-iii 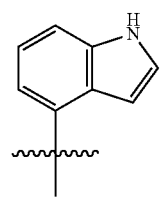
b-iv 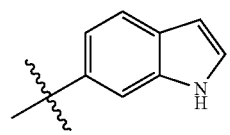
b-v 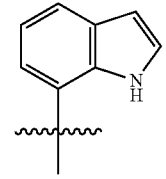
b-vi 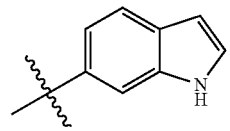
b-vii 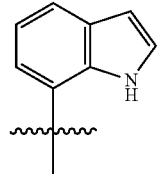
b-viii 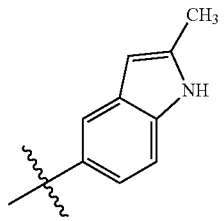
b-ix 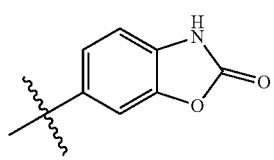
b-x 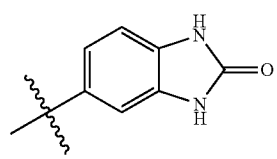
b-xi 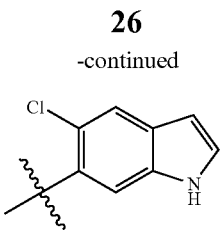
b-xii 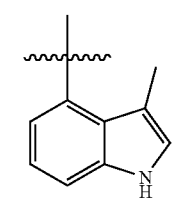
b-xiii 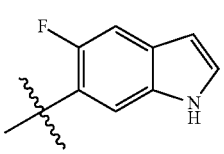
b-xiv 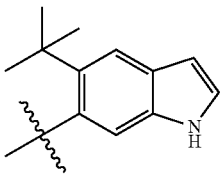
b-xv 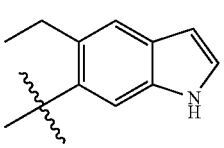
b-xvi 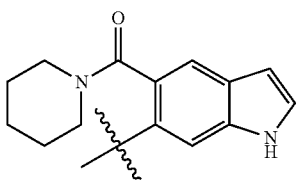
b-xvii 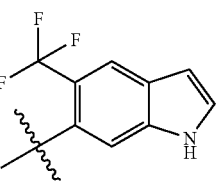
b-xviii 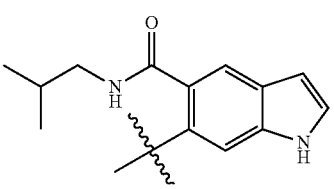
b-xix 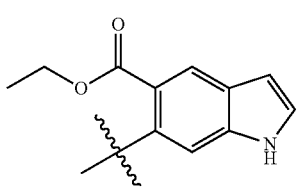

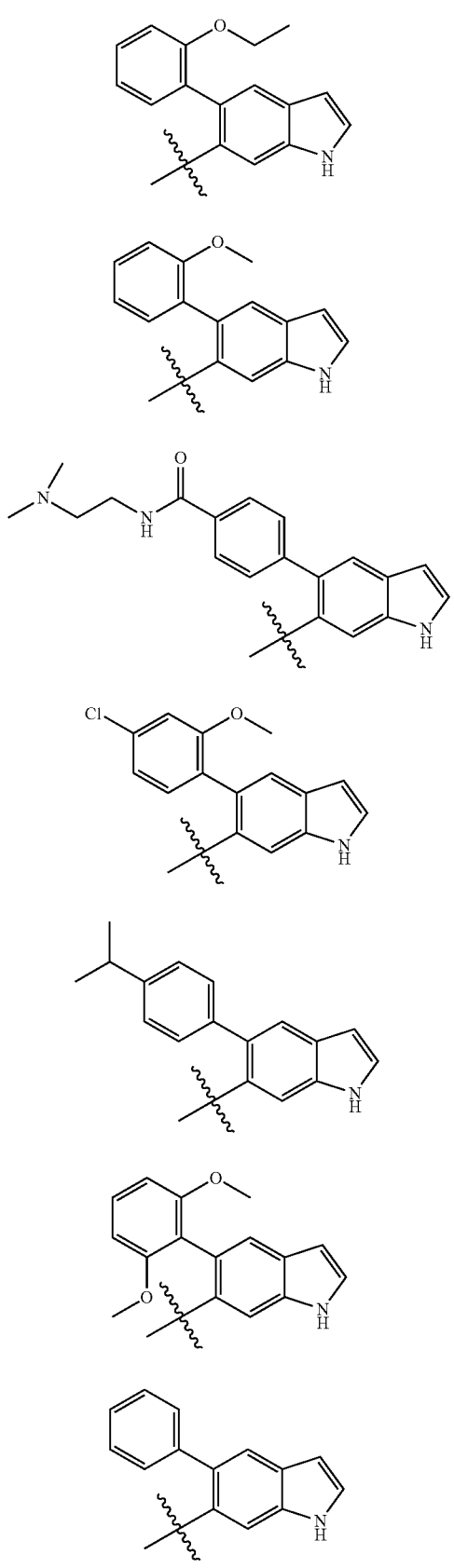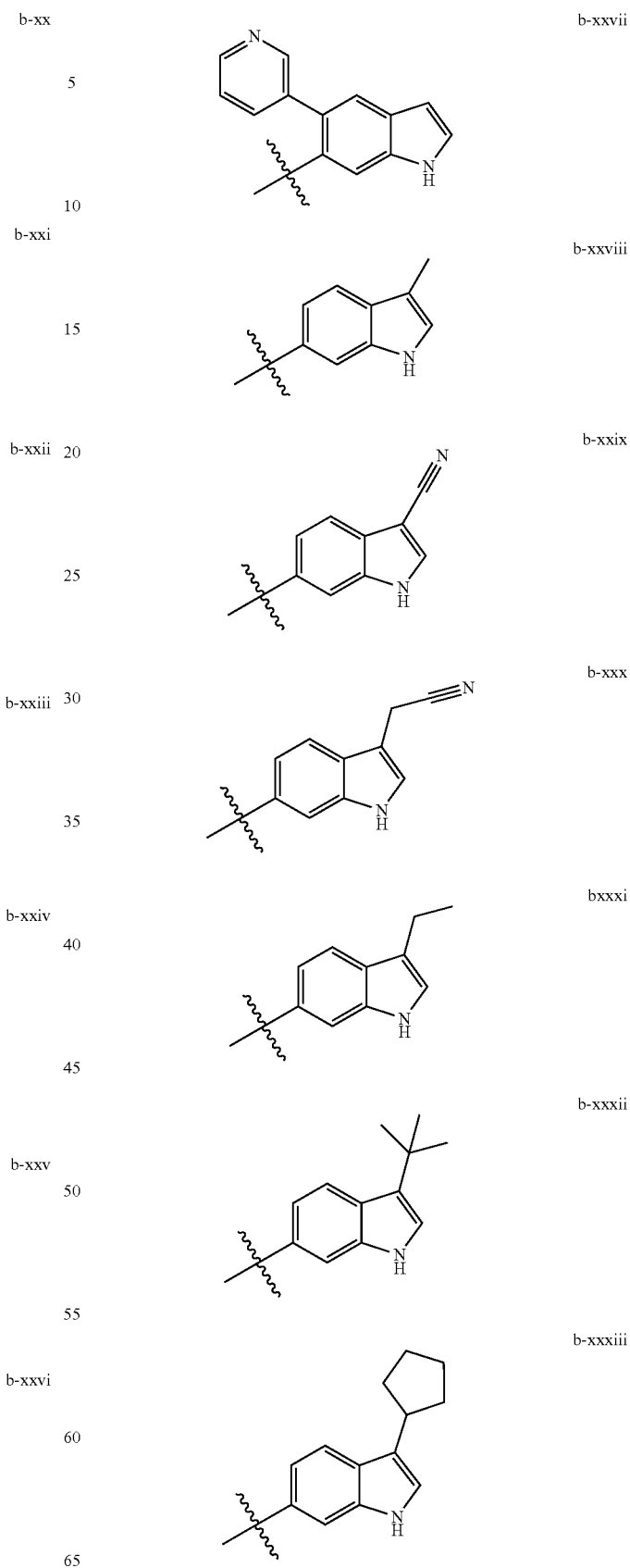

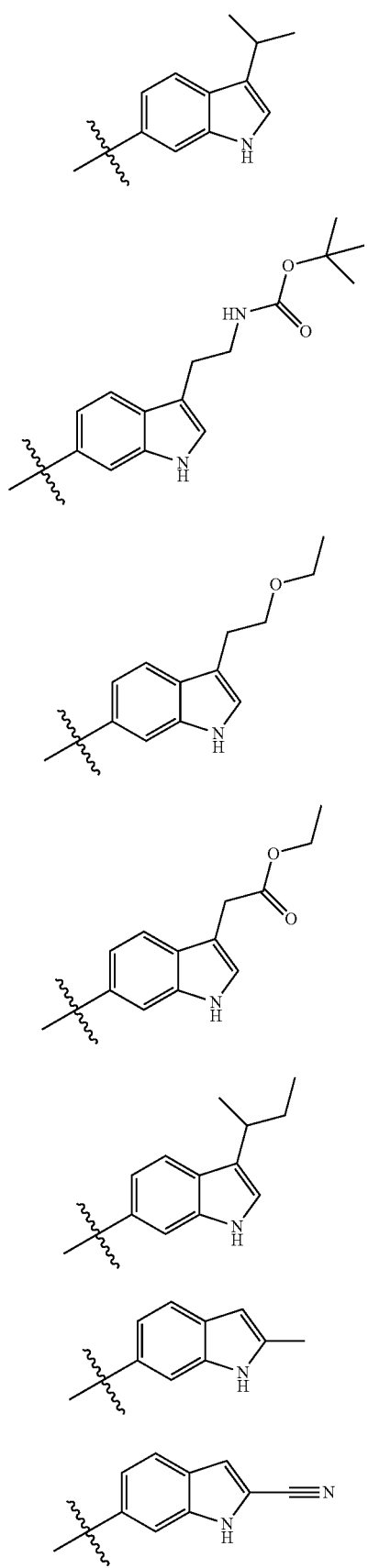
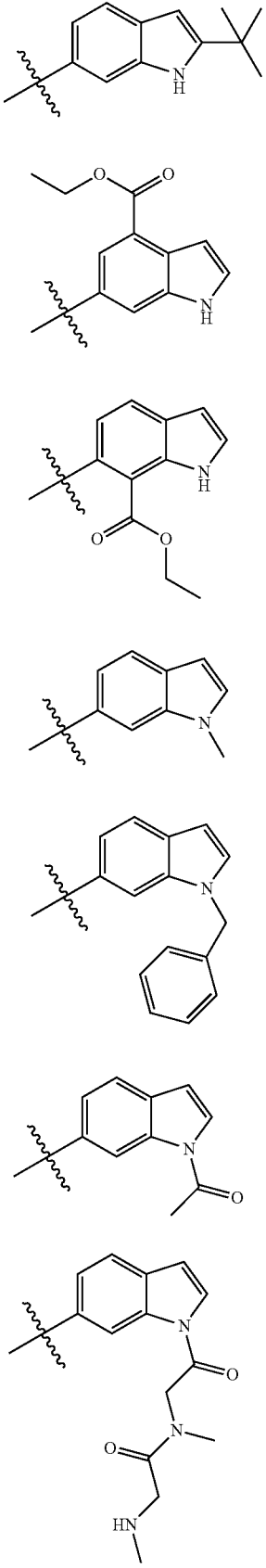

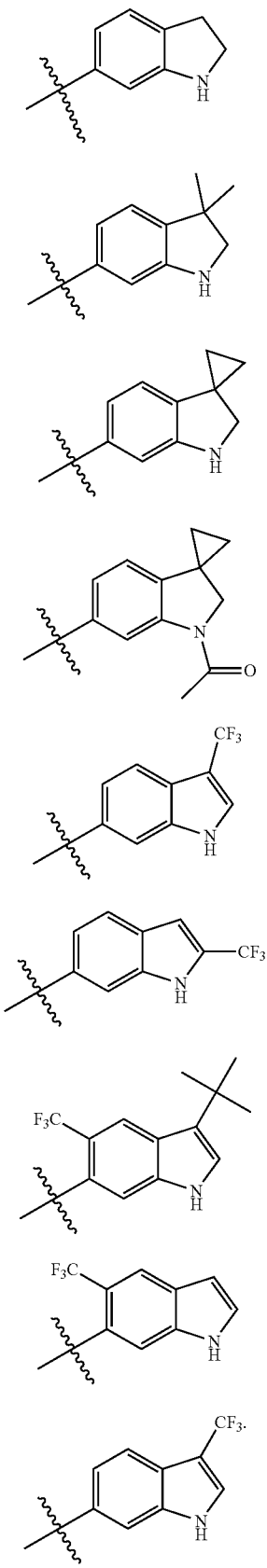

In some embodiments, $R^W$ is selected from halo, cyano, —$CF_3$, —$CHF_2$, —$OCHF_2$, -Me, -Et, —$CH(Me)_2$, —CHMeEt, n-propyl, t-butyl, —OMe, —OEt, —OPh, —O-fluorophenyl, —O-difluorophenyl, —O-methoxyphenyl, —O-tolyl, —O-benzyl, —SMe, —$SCF_3$, —$SCHF_2$, —SEt, —$CH_2CN$, —$NH_2$, —NHMe, —$N(Me)_2$, —NHEt, —$N(Et)_2$, —$C(O)CH_3$, —C(O)Ph, —$C(O)NH_2$, —SPh, —$SO_2$— (amino-pyridyl), —$SO_2NH_2$, —$SO_2Ph$, —$SO_2NHPh$, —$SO_2$—N-morpholino, —$SO_2$—N-pyrrolidyl, —N-pyrrolyl, —N-morpholino, 1-piperidyl, phenyl, benzyl, -(cyclohexyl-methylamino)methyl, 4-Methyl-2,4-di-hydro-pyrazol-3-one-2-yl, benzimidazol-2yl, furan-2-yl, 4-methyl-4H-[1,2,4]triazol-3-yl, 3-(4'-chlorophenyl)-[1,2,4] oxadiazol-5-yl, —NHC(O)Me, —NHC(O)Et, —NHC(O) Ph, or —$NHSO_2Me$ In some embodiments, X and $R^X$, taken together, is Me, Et, halo, —CN, —$CF_3$, —OH, —OMe, —OEt, —$SO_2N(Me)$ (fluorophenyl), —$SO_2$-(4-methyl-piperidin-1-yl, or —$SO_2$—N-pyrrolidinyl.

According to another embodiment, the present invention provides compounds of formula IVA.

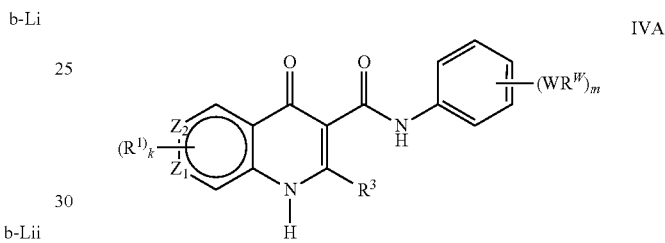

IVA

According to another embodiment, the present invention provides compounds of formula IVB:

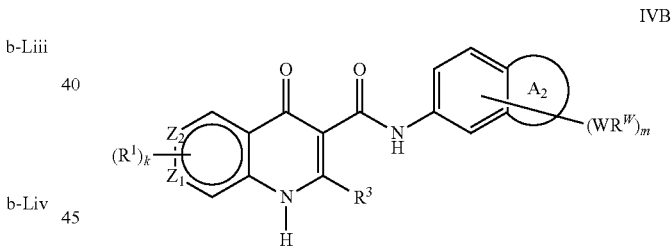

IVB

According to another embodiment, the present invention provides compounds of formula IVC.

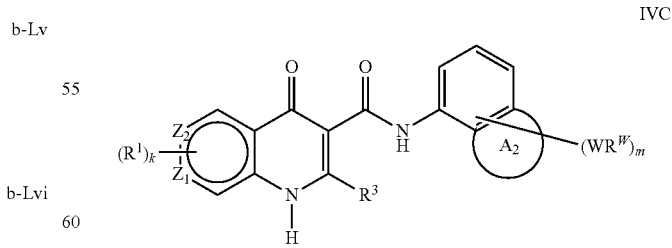

IVC

In one embodiment, the present invention provides compounds of formula IVA, formula IVA', formula IVB, formula IVB', formula IVC, wherein k is 1 or 2, and $R^1$ is H, Me, or halo. In another embodiment, k is 1 and $R^1$ is Me. In another embodiment, k is 2, and $R^1$ is Me.

In one embodiment, the present invention provides compounds of formula IVB, formula IVB', formula IVC, wherein ring $A_2$ is an optionally substituted, saturated, unsaturated, or aromatic seven membered ring with 0-3 heteroatoms selected from O, S, or N. Exemplary rings include azepanyl, 5,5-dimethyl azepanyl, etc.

In one embodiment, the present invention provides compounds of formula IVB or formula IVC, wherein ring $A_2$ is an optionally substituted, saturated, unsaturated, or aromatic six membered ring with 0-3 heteroatoms selected from O, S, or N. Exemplary rings include piperidinyl, 4,4-dimethylpiperidinyl, etc.

In one embodiment, the present invention provides compounds of formula IVB, formula IVB', formula IVC, wherein ring $A_2$ is an optionally substituted, saturated, unsaturated, or aromatic five membered ring with 0-3 heteroatoms selected from O, S, or N.

In one embodiment, the present invention provides compounds of formula IVB or formula IVC, wherein ring $A_2$ is an optionally substituted five membered ring with one nitrogen atom, e.g., pyrrolyl or pyrrolidinyl.

According to one embodiment of formula IVA, the following compound of formula VA-1 is provided.

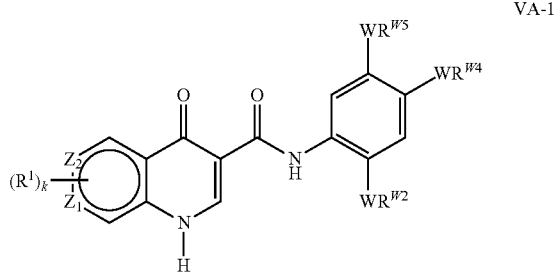

VA-1 wherein each of $WR^{W2}$ and $WR^{W4}$ is independently selected from hydrogen, —CN, —$CF_3$, —$OCF_3$, halo, $C_{1-6}$ straight or branched alkyl, 3-12 membered cycloaliphatic, phenyl, $C_{5-10}$ heteroaryl or $C_{3-7}$ heterocyclic, wherein said heteroaryl or heterocyclic has up to 3 heteroatoms selected from O, S, or N, wherein said $WR^{W2}$ and $WR^{W4}$ is independently and optionally substituted with up to three substituents selected from —OR', —$CF_3$, —$OCF_3$, SR', S(O)R', $SO_2R'$, —$SCF_3$, halo, —CN, —COOR', —COR', —O(CH$_2$)$_2$N(R')(R'), —O(CH$_2$)N(R')(R'), —CON(R')(R'), —(CH$_2$)$_2$OR', —(CH$_2$)OR', —CH$_2$CN, optionally substituted phenyl or phenoxy, —N(R')(R'), —NR'C(O)OR', —NR'C(O)R', —(CH$_2$)$_2$N(R')(R'), or —(CH$_2$)N(R')(R'); and $WR^{W5}$ is selected from hydrogen, halo, —OH, —NH$_2$, —CN, —CHF$_2$, —NHR', —N(R')$_2$, —NHC(O)R', —NHC(O)OR', —NHSO$_2$R', —OR', —CH$_2$OH, —CH$_2$N(R')$_2$, —C(O)OR', —C(O)N(R')$_2$, —SO$_2$NHR', —SO$_2$N(R')$_2$, —OSO$_2$N(R')$_2$, —OSO$_2$CF$_3$, or —CH$_2$NHC(O)OR'. Or, $WR^{W4}$ and $WR^{V5}$ taken together form a 5-7 membered ring containing 0-3 three heteroatoms selected from N, O, or S, wherein said ring is optionally substituted with up to three $WR^W$ substituents.

In one embodiment, the present invention provides compounds of formula VA-1, wherein k is 0.

In another embodiment, the present invention provides compounds of formula V-A-2:

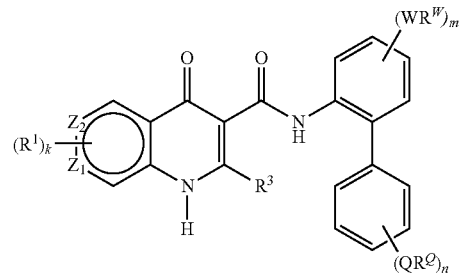

V-A-2 wherein:
Q is W;
$R^Q$ is $R^W$;
m is 0-4;
n is 0-4; and
$R^1$, k, W, and $R^W$ are as defined above.
In one embodiment, n is 0-2.
In another embodiment, m is 0-2. In one embodiment, m is 0. In one embodiment, m is 1. Or, m is 2.
In one embodiment, $QR^Q$ taken together is halo, —$CF_3$, —$OCF_3$, —CN, —$C_{1-6}$ aliphatic, —O—$C_{1-6}$ aliphatic, —O-phenyl, —NH($C_{1-6}$ aliphatic), or —N($C_{1-6}$ aliphatic)$_2$, wherein said aliphatic and phenyl are optionally substituted with up to three substituents selected from —$C_{1-6}$ alkyl, —O—$C_{1-6}$ alkyl, halo, cyano, —OH, or —$CF_3$, wherein up to two carbon units of said $C_{1-6}$ aliphatic or $C_{1-6}$ alkyl is optionally replaced with —CO—, —CONR'—, —CO$_2$—, —OCO—, —NR'CO$_2$—, —O—, —NR'CONR'—, —OCONR'—, —NR'CO—, —S—, —NR'—, —SOR', —SO$_2$R', —SO$_2$NR'—, —NR'SO$_2$—, or —NR'SO$_2$NR'—.
In another embodiment, R' above is $C_{1-4}$ alkyl.
Exemplary $QR^Q$ moieties include methyl, isopropyl, sec-butyl, hydroxymethyl, —$CF_3$, —NMe$_2$, —CN, —CH$_2$CN, fluoro, chloro, —OEt, —OMe, —SMe, —$OCF_3$, —OPh, —C(O)OMe, —C(O)O-iPr, —S(O)Me, —NHC(O)Me, or —S(O)$_2$Me.

In another embodiment, the present invention provides compounds of formula V-A-3:

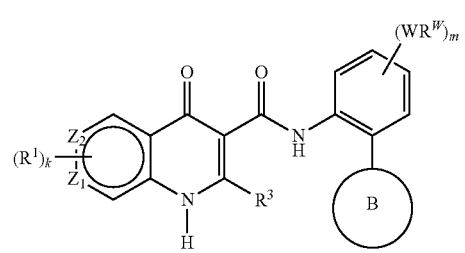

V-A-3 wherein:
ring B is a 5-7 membered monocyclic or bicyclic, heterocyclic or heteroaryl ring optionally substituted with up to n occurrences of -Q-$R^Q$, wherein n is 0-4, and Q and $R^Q$ are as defined above; and Q, $R^Q$, k, $R^1$, W, and $R^W$ are as defined above.

In one embodiment, m is 0-2. Or, m is 0. Or m is 1.
In one embodiment, n is 0-2. Or, n is 0. Or, n is 1.
In another embodiment, ring B is a 5-7 membered monocyclic, heterocyclic ring having up to 2 heteroatoms selected from O, S, or N, optionally substituted with up to n occurrences of -Q-$R^Q$. Exemplary heterocyclic rings include N-morpholinyl, N-piperidinyl, 4-benzoyl-piperazin-1-yl, pyrrolidin-1-yl, or 4-methyl-piperidin-1-yl.

In another embodiment, ring B is a 5-6 membered monocyclic, heteroaryl ring having up to 2 heteroatoms selected from O, S, or N, optionally substituted with up to n occurrences of -Q-$R^Q$. Exemplary such rings include benzimidazol-2-yl, 5-methyl-furan-2-yl, 2,5-dimethyl-pyrrol-1-yl, pyridine-4-yl, indol-5-yl, indol-2-yl, 2,4-dimethoxy-pyrimidin-5-yl, furan-2-yl, furan-3-yl, 2-acyl-thien-2-yl, benzothiophen-2-yl, 4-methyl-thien-2-yl, 5-cyano-thien-2-yl, 3-chloro-5-trifluoromethyl-pyridin-2-yl.

In another embodiment, the present invention provides compounds of formula V-B-1:

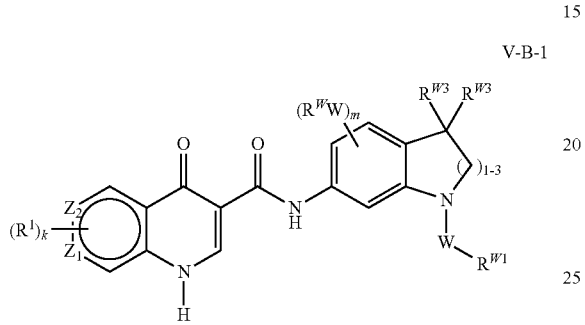

V-B-1 wherein:
$R^{W1}$ is hydrogen or $C_{1-6}$ aliphatic;
each of $R^{W3}$ is hydrogen or $C_{1-6}$ aliphatic; or
both $R^{W3}$ taken together form a $C_{3-6}$ cycloalkyl or heterocyclic ring having up to two heteroatoms selected from O, S, or NR', wherein said ring is optionally substituted with up to two $WR^W$ substituents;
m is 0-4; and
k, $R^1$, W, and $R^W$ are as defined above.

In one embodiment, $WR^{W1}$ is hydrogen, $C_{1-6}$ aliphatic, —C(O)—$C_{1-6}$ aliphatic, or —C(O)O—$C_{1-6}$ aliphatic.

In another embodiment, each $R^{W3}$ is hydrogen, $C_{1-4}$ alkyl. Or, both $R^{W3}$ taken together form a $C_{3-6}$ cycloaliphatic ring or 5-7 membered heterocyclic ring having up to two heteroatoms selected from O, S, or N, wherein said cycloaliphatic or heterocyclic ring is optionally substituted with up to three substitutents selected from $WR^{W1}$. Exemplary such rings include cyclopropyl, cyclopentyl, optionally substituted piperidyl, etc.

In another embodiment, the present invention provides compounds of formula V-B-2:

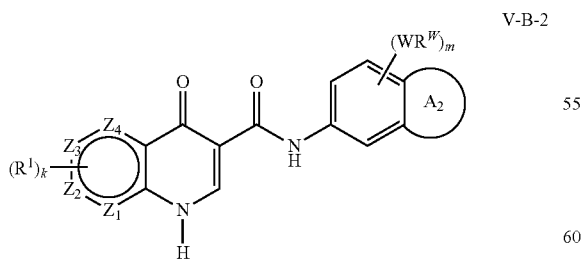

V-B-2 wherein:
ring $A_2$ is a phenyl or a 5-6 membered heteroaryl ring, wherein ring $A_2$ and the phenyl ring fused thereto together have up 4 substituents independently selected from $WR^W$;
m is 0-4; and
W, $R^W$, k, and $R^1$ are as defined above.

In one embodiment, ring $A_2$ is an optionally substituted 5-membered ring selected from pyrrolyl, furanyl, thienyl, pyrazolyl, imidazolyl, thiazolyl, oxazolyl, thiadiazolyl, oxadiazolyl, or triazolyl.

In one embodiment, ring $A_2$ is an optionally substituted 5-membered ring selected from pyrrolyl, pyrazolyl, thiadiazolyl, imidazolyl, oxazolyl, or triazolyl. Exemplary such rings include:

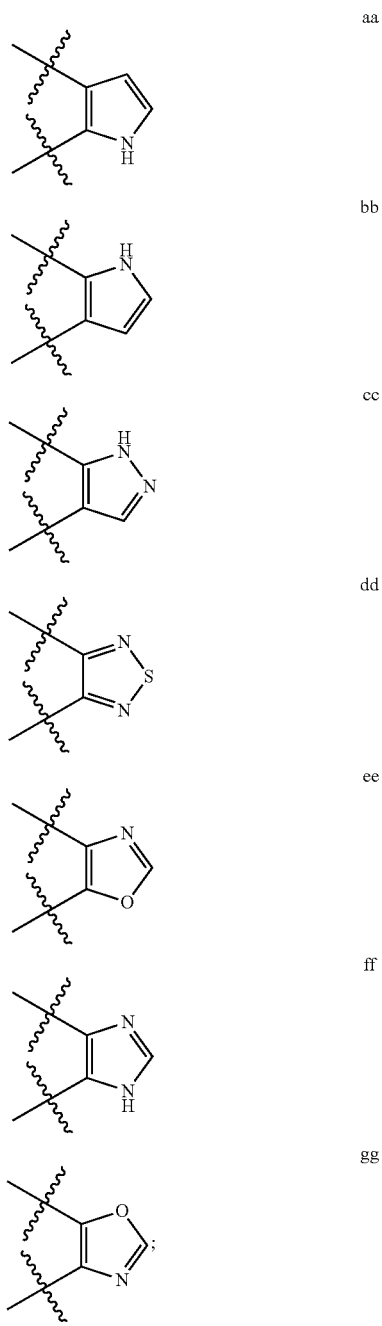

wherein said ring is optionally substituted as set forth above.

In another embodiment, ring $A_2$ is an optionally substituted 6-membered ring. Exemplary such rings include pyridyl, pyrazinyl, or triazinyl. In another embodiment, said ring is an optionally pyridyl.

In one embodiment, ring $A_2$ is phenyl.

In another embodiment, ring $A_2$ is pyrrolyl, pyrazolyl, pyridyl, or thiadiazolyl.

Examplary W in formula V-B-2 includes a bond, —C(O), —C(O)O or —$C_{1-6}$ alkylene.

Exemplary $R^W$ in formula V-B-2 include cyano, halo, $C_{1-6}$ aliphatic, $C_{3-6}$ cycloaliphatic, aryl, 5-7 membered heterocyclic ring having up to two heteroatoms selected from O, S, and N, wherein said aliphatic, phenyl, and heterocyclic are independently and optionally substituted with up to three substituents selected from —$C_{1-6}$ alkyl, —O—$C_{1-6}$ alkyl, halo, cyano, —OH, or —$CF_3$, wherein up to two methylene units of said $C_{1-6}$ aliphatic or $C_{1-6}$ alkyl is optionally replaced with —CO—, —CONR'—, —$CO_2$—, —COO—, —NR'$CO_2$—, —O—, —NR'CONR'—, —OCONR'—, —NR'CO—, —S—, —NR'—, —$SO_2$NR'—, —NR'$SO_2$—, or —NR'$SO_2$NR'—. In another embodiment, R' above is $C_{1-4}$ alkyl.

In one embodiment, the present invention provides compounds of formula V-B-3;

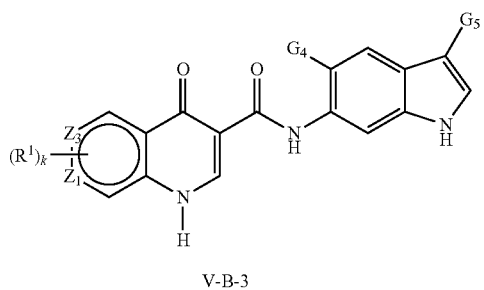

V-B-3 wherein:

$G_4$ is hydrogen, halo, —CN, —$CF_3$, —$CHF_2$, —$CH_2F$, optionally substituted $C_{1-6}$ aliphatic, aryl-$C_{1-6}$ alkyl, or a phenyl, wherein $G_4$ is optionally substituted with up to 4 $WR^W$ substituents; wherein up to two carbon units of said $C_{1-6}$ aliphatic or $C_{1-6}$ alkyl is optionally replaced with —CO—, —CONR'—, —$CO_2$—, —COO—, —NR'$CO_2$—, —O—, —NR'CONR'—, —OCONR'—, —NR'CO—, —S—, —NR'—, —$SO_2$NR'—, —NR'$SO_2$—, or —NR'$SO_2$NR'—;

$G_5$ is hydrogen, an optionally substituted $C_{1-6}$ aliphatic, —$CF_3$, or —CN;

wherein said indole ring system is further optionally substituted with up to 3 substituents independently selected from $WR^W$.

In one embodiment, $G_4$ is hydrogen. Or, $G_5$ is hydrogen.

In another embodiment, $G_4$ is hydrogen, and $G_5$ is $C_{1-6}$ aliphatic, —$CF_3$, or —CN, wherein said aliphatic is optionally substituted with $C_{1-6}$ alkyl, halo, cyano, or —$CF_3$, and wherein up to two carbon units of said $C_{1-6}$ aliphatic or $C_{1-6}$ alkyl is optionally replaced with —CO—, —CONR'—, —$CO_2$—, —COO—, —NR'$CO_2$—, —O—, —NR'CONR'—, —OCONR'—, —NR'CO—, —S—, —NR'—, —$SO_2$NR'—, —NR'$SO_2$—, or —NR'$SO_2$NR'—. In another embodiment, R' above is $C_{1-4}$ alkyl.

In another embodiment, $G_4$ is hydrogen, and $G_5$ is cyano, —$CF_3$, methyl, ethyl, propyl, isopropyl, butyl, sec-butyl, t-butyl, cyanomethyl, methoxyethyl, —$CH_2$C(O)OMe, —$(CH_2)_2$—NHC(O)O-tert-butyl, or cyclopentyl.

In another embodiment, $G_5$ is hydrogen, and $G_4$ is halo, $C_{1-6}$ aliphatic or phenyl, wherein said aliphatic or phenyl is optionally substituted with $C_{1-6}$ alkyl, halo, cyano, or —$CF_3$, wherein up to two carbon units of said $C_{1-6}$ aliphatic or $C_{1-6}$ alkyl is optionally replaced with —CO—, —CONR'—, —$CO_2$—, —COO—, —NR'$CO_2$—, —O—, —NR'CONR'—, —OCONR'—, —NR'CO—, —S—, —NR'—, —$SO_2$NR'—, —NR'$SO_2$—, or —NR'$SO_2$NR'—. In another embodiment, R' above is $C_{1-4}$ alkyl.

In another embodiment, $G_5$ is hydrogen, and $G_4$ is halo, —$CF_3$, ethoxycarbonyl, t-butyl, 2-methoxyphenyl, 2-ethoxyphenyl, (4-C(O)NH$(CH_2)_2$—$NMe_2$)-phenyl, 2-methoxy-4-chloro-phenyl, pyridine-3-yl, 4-isopropylphenyl, 2,6-dimethoxyphenyl, sec-butylaminocarbonyl, ethyl, t-butyl, or piperidin-1-ylcarbonyl.

In another embodiment, $G_4$ and $G_5$ are both hydrogen, and the nitrogen ring atom of said indole ring is substituted with $C_{1-6}$ aliphatic, C(O)($C_{1-6}$ aliphatic), or benzyl, wherein said aliphatic or benzyl is optionally substituted with $C_{1-6}$ alkyl, halo, cyano, or —$CF_3$, wherein up to two carbon units of said $C_{1-6}$ aliphatic or $C_{1-6}$ alkyl is optionally replaced with —CO—, —CONR'—, —$CO_2$—, —COO—, —NR'$CO_2$—, —O—, —NR'CONR'—, —OCONR'—, —NR'CO—, —S—, —NR'—, —$SO_2$NR'—, —NR'$SO_2$—, or —NR'$SO_2$NR'—. In another embodiment, R' above is $C_{1-4}$ alkyl.

In another embodiment, $G_4$ and $G_5$ are both hydrogen, and the nitrogen ring atom of said indole ring is substituted with acyl, benzyl, —C(O)$CH_2$N(Me)C(O)$CH_2$NHMe, or ethoxycarbonyl.

Representative compounds of the present invention are set forth below in Table 1 below.

TABLE 1

| Example. No. | Name | Structure |
|---|---|---|
| 1 | N-benzhydryl-4-oxo-1,4-dihydro-1,6-naphthyridine-3-carboxamide | 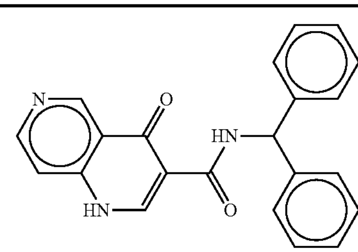 |

TABLE 1-continued

| Example. No. | Name | Structure |
|---|---|---|
| 2 | N-(2,2-diphenylethyl)-4-oxo-1,4-dihydro-1,6-naphthyridine-3-carboxamide | 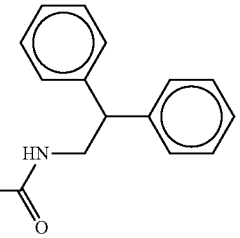 |
| 3 | 4-oxo-N-(2-propylphenyl)-1,4-dihydro-1,6-naphthyridine-3-carboxamide | 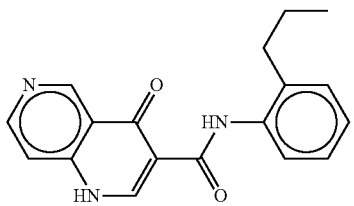 |
| 4 | N-(2-isopropylphenyl)-4-oxo-1,4-dihydro-1,6-naphthyridine-3-carboxamide | 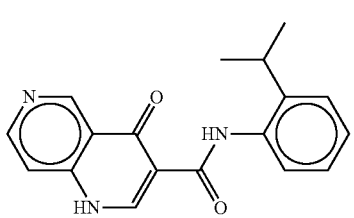 |
| 5 | N-(biphenyl-2-yl)-4-oxo-1,4-dihydro-1,6-naphthyridine-3-carboxamide | 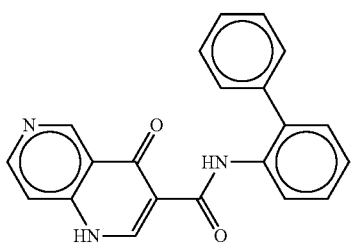 |
| 6 | N-(1H-indol-6-yl)-4-oxo-1,4-dihydro-1,6-naphthyridine-3-carboxamide | 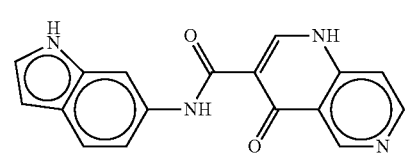 |
| 7 | 4-oxo-N-(4-(pyrrolidin-1-yl)-2-(trifluoromethyl)phenyl)-1,4-dihydro-1,6-naphthyridine-3-carboxamide | 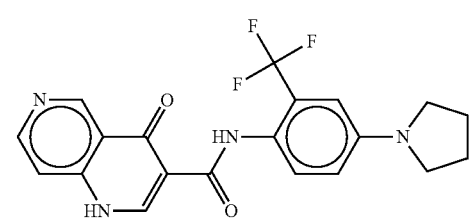 |
| 8 | 4-oxo-N-((1-(4-(trifluoromethoxy)phenyl)-cyclopentyl)methyl)-1,4-dihydro-1,6-naphthyridine-3-carboxamide | 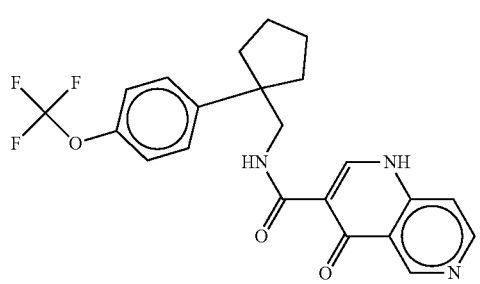 |

TABLE 1-continued

| Example. No. | Name | Structure |
|---|---|---|
| 9 | N-(2,4-di-tert-butyl-5-hydroxyphenyl)-4-oxo-1,4-dihydro-1,7-naphthyridine-3-carboxamide | 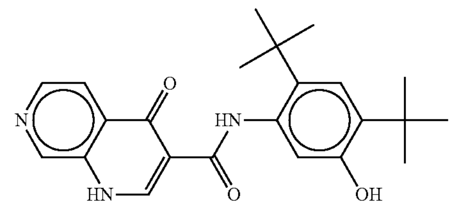 |
| 10 | N-(5-tert-butyl-1H-indol-6-yl)-4-oxo-1,4-dihydro-1,7-naphthyridine-3-carboxamide | 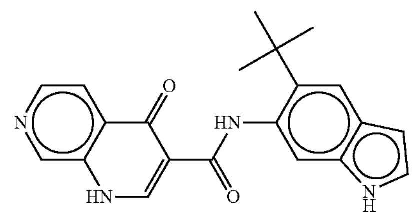 |
| 11 | 4-oxo-N-(4-(pyrrolidin-1-yl)-2-(trifluoromethyl)phenyl)-1,4-dihydro-1,7-naphthyridine-3-carboxamide | 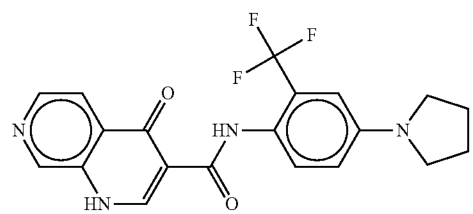 |
| 12 | (S)-N-(4-(2-methylpyrrolidin-1-yl)-2-(trifluoromethyl)phenyl)-4-oxo-1,4-dihydro-1,7-naphthyridine-3-carboxamide | 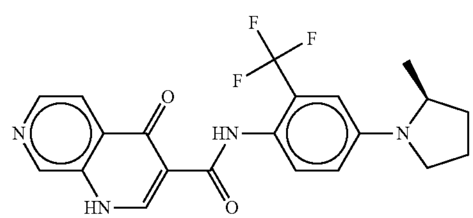 |
| 13 | N-(2-fluoro-5-hydroxy-4-(1-methylcyclohexyl)phenyl)-4-oxo-1,4-dihydro-1,7-naphthyridine-3-carboxamide | 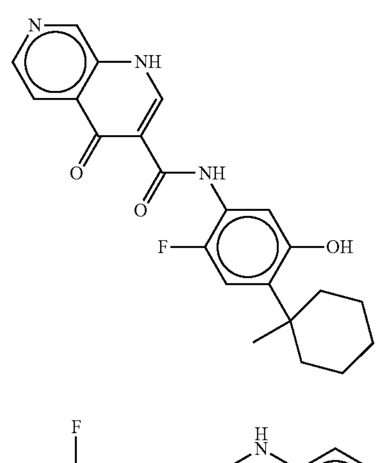 |
| 14 | 4-oxo-N-(5-(trifluoromethyl)-1H-indol-6-yl)-1,4-dihydro-1,7-naphthyridine-3-carboxamide | 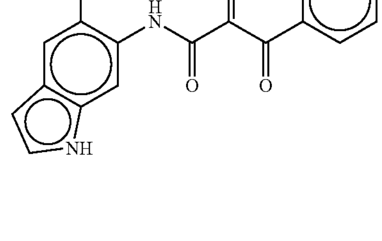 |

TABLE 1-continued

| Example. No. | Name | Structure |
|---|---|---|
| 15 | 6-methyl-4-oxo-N-(5-(trifluoromethyl)-1H-indol-6-yl)-1,4-dihydro-1,7-naphthyridine-3-carboxamide | 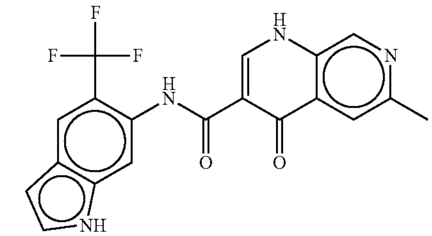 |
| 16 | 4-oxo-N-(3-(trifluoromethyl)-1H-indol-6-yl)-1,4-dihydro-1,7-naphthyridine-3-carboxamide | 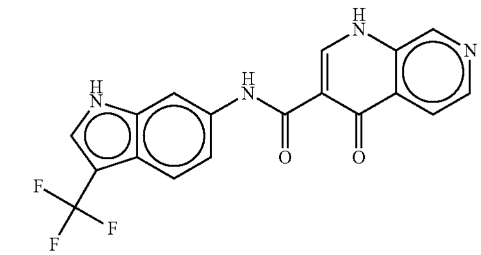 |
| 17 | N-(2-fluoro-5-hydroxy-4-(1-methylcyclohexyl)phenyl)-6-methyl-4-oxo-1,4-dihydro-1,7-naphthyridine-3-carboxamide | 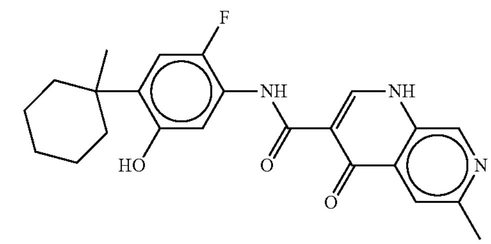 |
| 18 | N-(4-(3,3-dimethylpiperidin-1-yl)-2-(trifluoromethyl)phenyl)-4-oxo-1,4-dihydro-1,7-naphthyridine-3-carboxamide | 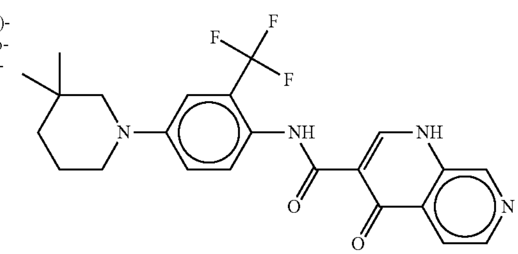 |

4. General Synthetic Schemes

Compounds of the present invention are prepared by methods known in the art and as illustrated in the schemes below which are exemplary methods for the preparation of compounds of the present invention.

In one method, naphthyiridine carboxylic acids are prepared as illustrated in Scheme 1.

Scheme 1:

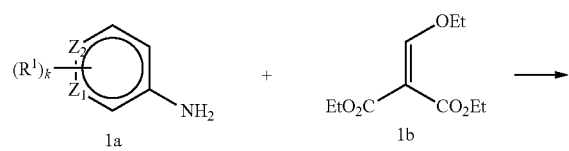

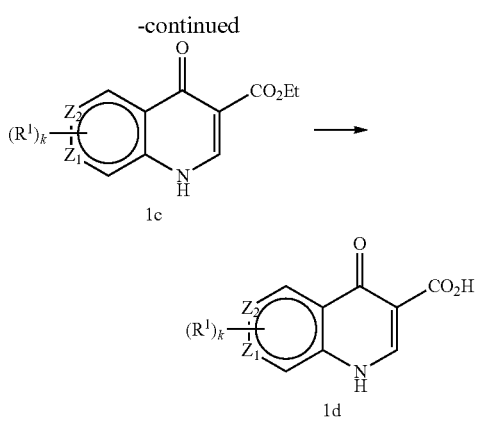

Referring to Scheme 1, an aminopyridine 1a reacts with the ethylidene ester 1b at elevated temperatures in an inert solvent such as, for example, Dowtherm® A to provide the naphthyridine ester 1c. Hydrolysis of 1c with, for example, aqueous sodium hydroxide provides the naphthyridine acid 1d.

In an another method, 1,7-naphthyiridine carboxylic acids may be prepared using an aminopyridine-3-N-oxide as illustrated in Scheme 2.

Scheme 2:

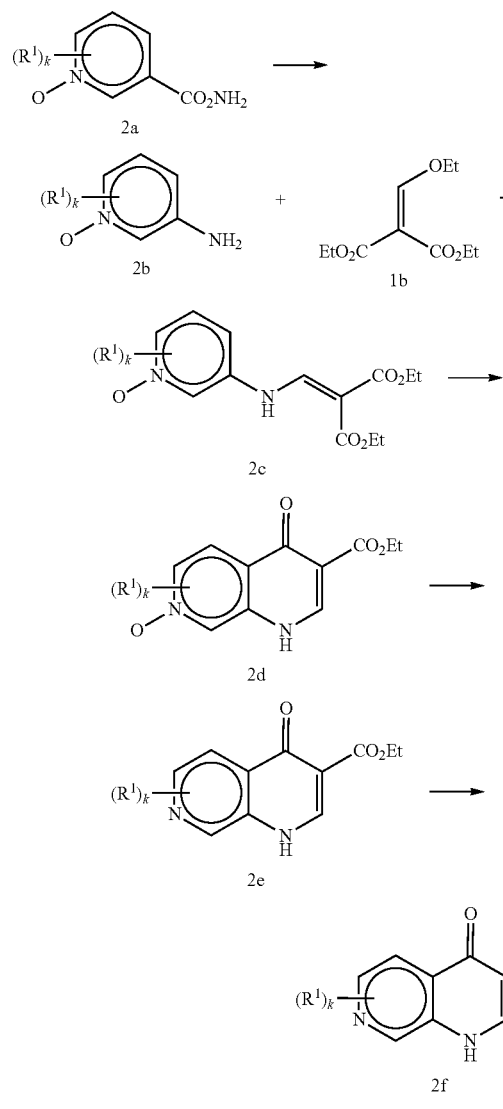

Referring to Scheme 2, the pyridine-n-oxide carboxamide 2a undergoes Hofmann rearrangement by oxidation with, for example, sodium hypochorite to provide the amine 2b. Reaction of 2b with the ethylidene ester 1b provides the intermediate 2c which is cyclized at levated temperature as previously described to provide the naphthyridine 2d. Reduction of the N-oxide 2d with, for example, iron in the presence of acetic acid, provides the ester 2e. Hydrolysis of 2e with aqueous sodium hydroxide provides the desired naphthyridine acid 2f. Naphthyridine carboxamides of the present invention may be prepared from naphthyiridine carboxylic acids as illustrated in Scheme 3.

Scheme 3:

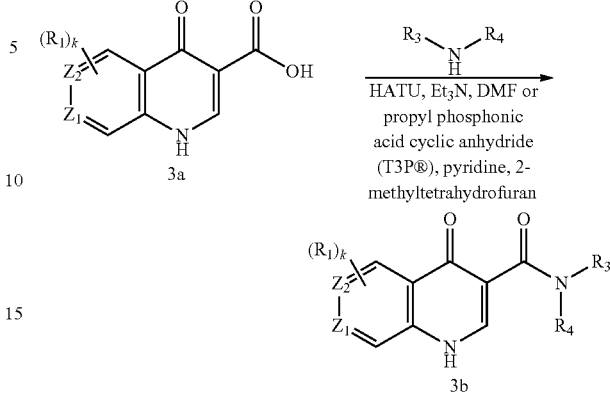

Referring to Scheme 3, acid 3a can be reacted with any amine to form amide (3b) using coupling reagents such as HATU (2-(1H-7-Azabenzotriazol-1-yl)-1,1,3,3-tetramethyl uronium hexafluorophosphate methanaminium) or T3P (2-propanephosphonic acid anhydride) in the presence of a base.

Amino-phenols are commercially available or may be prepared from suitable phenol starting materials using known methodologies. Such methodlogies include, for example, halogenation, nitration, alkylation and Suzuki couplings. One example of such a synthetic strategy is outlined in Scheme 4.

Scheme 4:

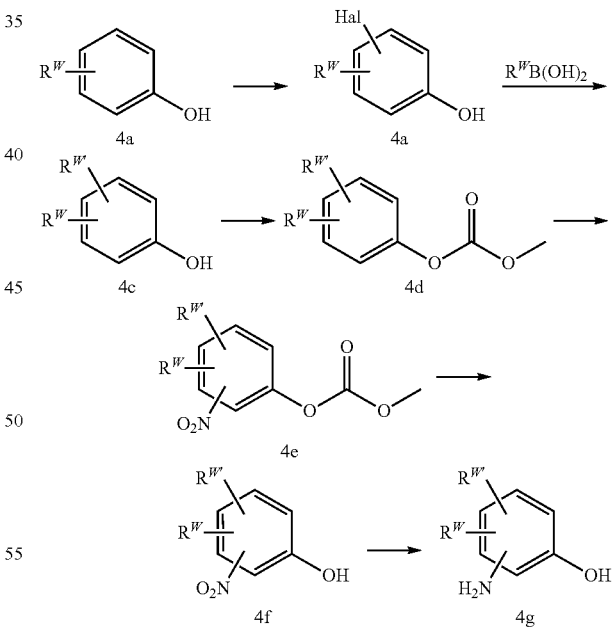

Referring to Scheme 4, a phenol 4a may be halogenated to provide the halophenol 4b. A Suzuki coupling with a suitable aryl boronic acid provides the intermediate 4c wherein $R^{W'}$ is, for example an aryl moiety. The intermediate 4e may be protected as the methyl carbonate 4d. Nitration of 4d under known conditions provides the nitro compound 4e. Deprotection of 3e gives the nitrophenol 4f which is reduced to the amino phenol 4 g.

Alternatively, certain alkyl phenols may be prepared by alkylation of a phenol as illustrated in Scheme 5.

Scheme 5:

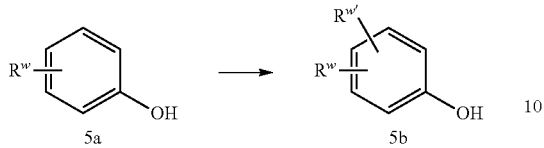

Referring to Scheme 5, a phenol 5a may be alkylated with a tertiary alcohol in the presence of a strong acid such as, for example, sulfuric acid to provide the intermediate 5b wherein $R^{W''}$ is a tertiary alkyl moiety. Preparation of the corresponding amino phenol follows the steps as described for 4c.

Certain amino-indoles may be prepared as illustrated in Scheme 6.

Scheme 6:

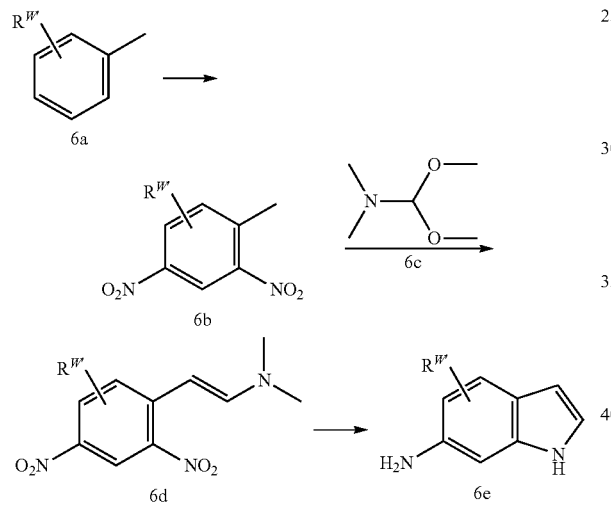

Referring to Scheme 6, a suitably substituted toluene 6a is nitrated to provide the dinitro compound 6b. Reaction of 5b with the amino-acetal 6c provides the dinitro compound 6d. Reduction of 6d provides the amino-indole 6e.

5-Trifluormethyl-1H-indol-6-ylamine may be prepared using procedures as described by Hadida Ruah, S. S. et al., "Modulators of ATP-Binding Cassette Transporters," PCT application Number WO 2006/002421.

An alternative method for preparing amino-indoles is illustrated in Scheme 7.

Scheme 6:

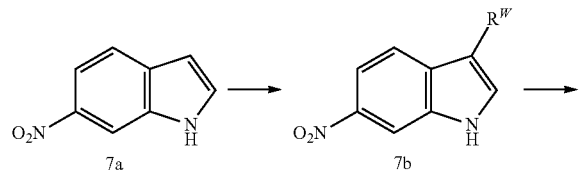

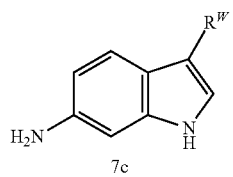

Referring to Scheme 7, the nitroindole 7a is alkylated with an appropriate $R^W$ iodide or bromide in the presence of zinc triflate, TBAI and DIEA to give the intermediate 6b. Reduction of the nitro group of 7b provides the amino-indole 7c.

A further method for the preparation of amino-indoles is illustrated in Scheme 8.

Scheme 8:

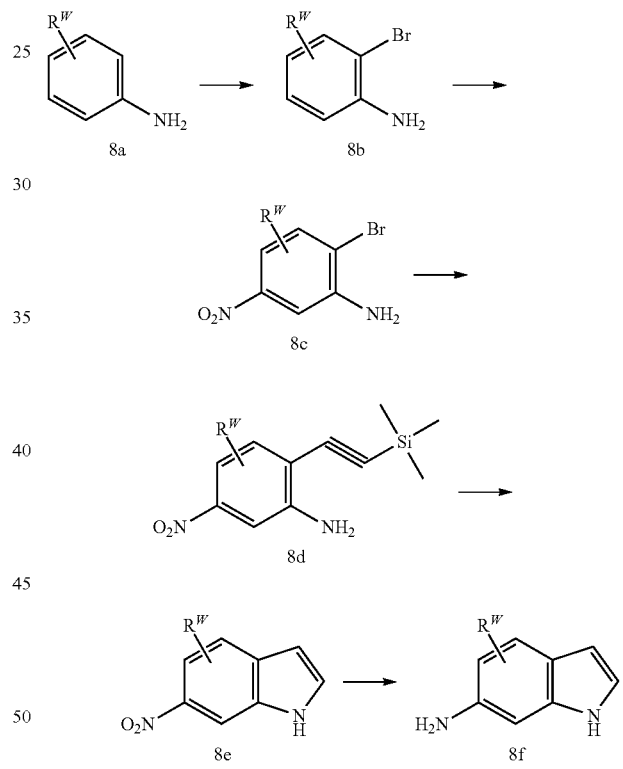

Referring to Scheme 8, an aniline 8a is brominated with, for example, NBS in DMF to provide the bromo-aniline 8b. Nitration of 8b provides the nitro intermediate 8d. Reaction of 8d with trimethylsilylacetylene in the presence of a palladium catalyst, copper iodied and a tertiary amine provides the intermediate 8d. Ring closure of 8d using, for example, copper iodide provides the nito-indole 8e. Reduction of the nitro group of 8e provides the desired amino-indole 8f.

Anilines are commercially available or may be prepared from suitable nitrobenzene starting materials using known methodologies. One example of such a synthetic strategy is outlined in Scheme 9.

Scheme 9:

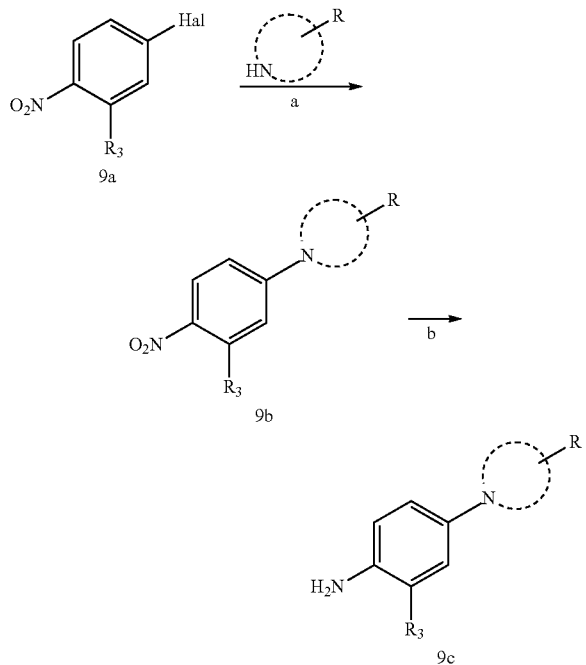

a) DMSO, K2CO₃, heat or CH₃CN, TEA, heat; (b) H₂, Pd/C, EtOH

Referring to Scheme 9, the halogen moiety of nitro compound 9a is displaced with an amine in the presence of base to give nitro compound 9b. The nitro group is then subsequently reduced with hydrogen in the presence of a palladium catalyst to give aniline 9c.

Alkylamines are commercially available or may be prepared from suitable starting materials using known methodologies. One example of such a synthetic strategy is outlined in Scheme 10.

Scheme 10:

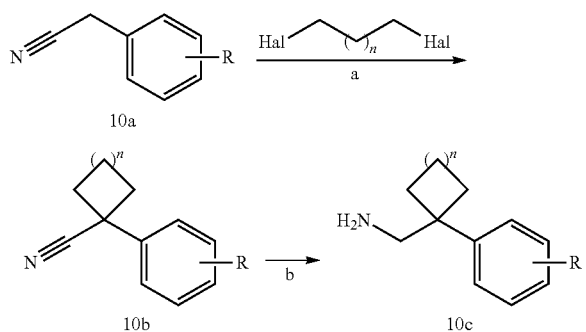

a) NaH, THF; (b) LiAlH₄, Et₂O

Referring to Scheme 10, nitrile 10a is treated with a dihalogenated alkane in the presence of a base to give nitrile 10b. The nitrile group is subsequently reduced to give amine 10c.

5. Uses, Formulation and Administration

Pharmaceutically Acceptable Compositions

As discussed above, the present invention provides compounds that are useful as modulators of ABC transporters and thus are useful in the treatment of disease, disorders or conditions such as cystic fibrosis, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders asuch as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease.

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative or a prodrug thereof. According to the present invention, a pharmaceutically acceptable derivative or a prodrug includes, but is not limited to, pharmaceutically acceptable salts, esters, salts of such esters, or any other adduct or derivative which upon administration to a patient in need thereof is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof.

Pharmaceutically acceptable salts are well known in the art. For example, S. M. Berge, et al. describes pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except, insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, the present invention provides a method of treating a condition, disease, or disorder implicated by ABC transporter activity, e.g., CFTR. In certain embodiments, the present invention provides a method of treating a condition, disease, or disorder implicated by a deficiency of the ABC transporter activity, the method comprising administering a composition comprising a compound of formula (I) to a subject, preferably a mammal, in need thereof.

In certain embodiments, the present invention provides a method of treating cystic fibrosis, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders asuch as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease, comprising the step of administering to said mammal an effective amount of a composition comprising a compound of the present invention.

According to an alternative preferred embodiment, the present invention provides a method of treating cystic fibrosis comprising the step of administering to said mammal a composition comprising the step of administering to said mammal an effective amount of a composition comprising a compound of the present invention.

According to the invention an "effective amount" of the compound or pharmaceutically acceptable composition is that amount effective for treating or lessening the severity of one or more of cystic fibrosis, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders asuch as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease.

The compounds and compositions, according to the method of the present invention, may be administered using any amount and any route of administration effective for treating or lessening the severity of one or more of cystic fibrosis, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders asuch as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease.

In one embodiment, the compounds and compositions of the present invention are useful for treating or lessening the severity of cystic fibrosis in a patient.

In certain embodiments, the compounds and compositions of the present invention are useful for treating or lessening the severity of cystic fibrosis in patients who exhibit residual CFTR activity in the apical membrane of respiratory and non-respiratory epithelia. The presence of residual CFTR activity at the epithelial surface can be readily detected using methods known in the art, e.g., standard electrophysiological, biochemical, or histochemical techniques. Such methods identify CFTR activity using in vivo or ex vivo electrophysiological techniques, measurement of sweat or salivary Cl⁻ concentrations, or ex vivo biochemical or histochemical techniques to monitor cell surface density. Using such methods, residual CFTR activity can be readily detected in patients heterozygous or homozygous for a variety of different mutations, including patients homozygous or heterozygous for the most common mutation, ΔF508.

In another embodiment, the compounds and compositions of the present invention are useful for treating or lessening the severity of cystic fibrosis in patients who have residual CFTR activity induced or augmented using pharmacological methods or gene therapy. Such methods increase the amount of CFTR present at the cell surface, thereby inducing a hitherto absent CFTR activity in a patient or augmenting the existing level of residual CFTR activity in a patient.

In one embodiment, the compounds and compositions of the present invention are useful for treating or lessening the severity of cystic fibrosis in patients within certain genotypes exhibiting residual CFTR activity, e.g., class III mutations (impaired regulation or gating), class IV mutations (altered conductance), or class V mutations (reduced synthesis) (Lee R. Choo-Kang, Pamela L., Zeitlin, Type I, II, III, IV, and V cystic fibrosis Tansmembrane Conductance Regulator Defects and Opportunities of Therapy; Current Opinion in Pulmonary Medicine 6:521-529, 2000). Other patient genotypes that exhibit residual CFTR activity includes patients homozygous for one of these classes or heterozygous with any other class of mutations, including class I mutations, class II mutations, or a mutation that lacks classification.

In one embodiment, the compounds and compositions of the present invention are useful for treating or lessening the severity of cystic fibrosis in patients within certain clinical phenotypes, e.g., a moderate to mild clinical phenotype that typically correlates with the amount of residual CFTR activity in the apical membrane of epithelia. Such phenotypes include patients exhibiting pancreatic sufficiency or patients diagnosed with idiopathic pancreatitis and congenital bilateral absence of the vas deferens, or mild lung disease.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as modulators of ABC transporters. Thus, without wishing to be bound by any particular theory, the compounds and compositions are particularly useful for treating or lessening the severity of a disease, condition, or disorder where hyperactivity or inactivity of ABC transporters is implicated in the disease, condition, or disorder. When hyperactivity or inactivity of an ABC transporter is implicated in a particular disease, condition, or disorder, the disease, condition, or disorder may also be referred to as a "ABC transporter-mediated disease, condition or disorder". Accordingly, in another aspect, the present invention provides a method for treating or lessening the severity of a disease, condition, or disorder where hyperactivity or inactivity of an ABC transporter is implicated in the disease state.

The activity of a compound utilized in this invention as a modulator of an ABC transporter may be assayed according to methods described generally in the art and in the Examples herein.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

In one embodiment, the additional agent is selected from a mucolytic agent, bronchodialator, an anti-biotic, an anti-infective agent, an anti-inflammatory agent, a CFTR modulator other than a compound of the present invention, or a nutritional agent.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to modulating ABC transporter activity in a biological sample or a patient (e.g., in vitro or in vivo), which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of ABC transporter activity, e.g., CFTR, in a biological sample is useful for a variety of purposes that are known to one of skill in the art. Examples of such purposes include, but are not limited to, the study of ABC transporters in biological and pathological phenomena; and the comparative evaluation of new modulators of ABC transporters.

In yet another embodiment, a method of modulating activity of an anion channel in vitro or in vivo, is provided comprising the step of contacting said channel with a compound of formula (I). In preferred embodiments, the anion channel is a chloride channel or a bicarbonate channel. In other preferred embodiments, the anion channel is a chloride channel.

According to an alternative embodiment, the present invention provides a method of increasing the number of functional ABC transporters in a membrane of a cell, comprising the step of contacting said cell with a compound of formula (I). The term "functional ABC transporter" as used herein means an ABC transporter that is capable of transport activity. In preferred embodiments, said functional ABC transporter is CFTR.

According to another preferred embodiment, the activity of the ABC transporter is measured by measuring the transmembrane voltage potential. Means for measuring the voltage potential across a membrane in the biological sample may employ any of the known methods in the art, such as optical membrane potential assay or other electrophysiological methods.

The optical membrane potential assay utilizes voltage-sensitive FRET sensors described by Gonzalez and Tsien (See, Gonzalez, J. E. and R. Y. Tsien (1995) "Voltage sensing by fluorescence resonance energy transfer in single cells" Biophys J 69(4): 1272-80, and Gonzalez, J. E. and R. Y. Tsien (1997) "Improved indicators of cell membrane potential that use fluorescence resonance energy transfer" Chem Biol 4(4): 269-77) in combination with instrumentation for measuring fluorescence changes such as the Voltage/Ion Probe Reader (VIPR) (See, Gonzalez, J. E., K. Oades, et al. (1999) "Cell-based assays and instrumentation for screening ion-channel targets" Drug Discov Today 4(9): 431-439).

These voltage sensitive assays are based on the change in fluorescence resonant energy transfer (FRET) between the membrane-soluble, voltage-sensitive dye, $DiSBAC_2(3)$, and a fluorescent phospholipid, CC2-DMPE, which is attached to the outer leaflet of the plasma membrane and acts as a FRET donor. Changes in membrane potential ($V_m$) cause the negatively charged $DiSBAC_2(3)$ to redistribute across the plasma membrane and the amount of energy transfer from CC2-DMPE changes accordingly. The changes in fluorescence emission can be monitored using VIPR™ II, which is an integrated liquid handler and fluorescent detector designed to conduct cell-based screens in 96- or 384-well microtiter plates.

In another aspect the present invention provides a kit for use in measuring the activity of a ABC transporter or a fragment thereof in a biological sample in vitro or in vivo comprising (i) a composition comprising a compound of formula (I) or any of the above embodiments; and (ii) instructions for a) contacting the composition with the biological sample and b) measuring activity of said ABC transporter or a fragment thereof. In one embodiment, the kit further comprises instructions for a) contacting an additional composition with the biological sample; b) measuring the activity of said ABC transporter or a fragment thereof in the presence of said additional compound, and c) comparing the activity of the ABC transporter in the presence of the additional compound with the density of the ABC transporter in the presence of a composition of formula (I). In preferred embodiments, the kit is used to measure the density of CFTR.

In order that the invention described herein may be more fully understood, the following examples are set forth. It should be understood that these examples are for illustrative purposes only and are not to be construed as limiting this invention in any manner.

PREPARATIONS AND EXAMPLES

A. Preparation of Naphthyridine Carboxylic Acids

Preparation 1:
4-Hydroxy-1,6-naphthyridine-3-carboxylic acid

Step 1: Ethyl 4-hydroxy-1,6-naphthyridine-3-carboxylate

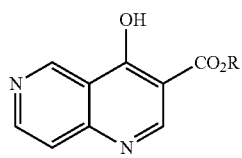

To Dowtherm A (150 mL) was added 3-aminopyridine (4.8 g, 50 mmol) and diethyl 2-(ethoxymethylene)malonate (4.8 g, 50 mmol). The mixture was stirred and heated to 150° C. until the alcohol was removed by distillation. The reaction mixture was then refluxed for 1 hour, cooled to room temperature and the precipitate was removed by filtration and washed with petroleum ether to the title compound (2.6 g) as a brown powder.

Step 2: 4-Hydroxy-1,6-naphthyridine-3-carboxylic acid

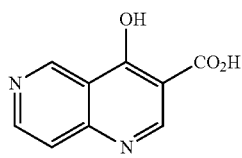 [SMILES: O=C(O)c1cnc2ccncc2c1O]

Ethyl 4-hydroxy-1,6-naphthyridine-3-carboxylate (2.6 g, 11 mmol) was refluxed for six hours with sodium hydroxide (25 mL, 4%). The hot solution was decolorized with charcoal, filtered and acidified to pH 3. After cooling, the precipitate was removed by filtration, washed with water and dried to give the title compound (1.3 g) as a tan powder. $^1$H NMR (DMSO_$d_6$): δ: 14.66 (s, 1H), 12.8-14 (br, 1H), 9.42 (s, 1H), 8.98 (s, 1H), 8.80 (d, J=5.6, 1H), 7.69 (d, J=5.6, 1H), MS (ESI) m/e (M+H$^+$) 191.12.

Preparation 2:
4-Oxo-1,4-dihydro-1,7-naphthyridine-3-carboxylic acid

Step 1: Diethyl 3-aminopyridine 1-oxide

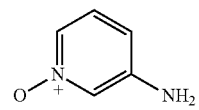

To a solution of NaOCl (9.0%, 100.0 mL) was added NaOH (9.3 g, 232 mmol). The mixture was stirred in ice bath until a solution was obtained. Then to the mixture was added nicotinamide-N-oxide (8.0 g, 58.0 mmol) and the reaction was stirred for 15 minutes at room temperature. Then the mixture was heated to 90° C. until a deep burgundy color was observed. Then the reaction was cooled to room temperature and adjusted to pH 2 with conc. HCl which evaporated to dryness at reduced pressure. The residue was extracted with hot ethanol (50×6 mL). The extract was combined, dried over Na$_2$SO$_4$ and concentrated in vacuo. The crude product was purified by silica column chromatography (methanol/CH$_2$Cl$_2$, 5%) to give the title compound (3.0 g). $^1$H NMR (400 MHz, MeOD) δ 7.75-7.74 (m, 1H), 7.58 (dd, J=1.2, 6.4 Hz, 1H), 7.21-7.18 (m, 1H), 6.91 (dd, J=1.6, 8.4 Hz, 1H).

Step 2: 3-(3-ethoxy-2-(ethoxycarbonyl)-3-oxoprop-1-enylamino)pyridine 1-oxide

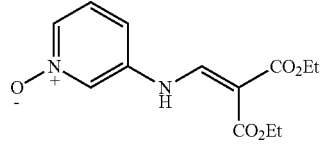

A mixture of diethyl 3-aminopyridine 1-oxide (3.0 g, 27.3 mmol) and diethyl 2-(ethoxymethylene)malonate (11.8 g, 54.6 mmol) was heated to 130° C. under a Dean-Stark trap for 2 hours. After cooling to room temperature, the mixture was stirred with ethanol (100 mL). The solid was collected by filtration, washed with petroleum ether (100 mL) and dried in vacuo to afford the title compound (6.0 g). $^1$H NMR (400 MHz, MeOD) δ 8.40-8.39 (t, J=1.6 Hz, 1H), 8.36 (s, 1H), 8.01

(d, J=6.4 Hz, 1H), 7.49 (d, J=1.2 Hz, 1H), 7.46-7.44 (m, 1H), 4.22 (q, J=7.2 Hz, 2H), 4.14 (q, J=7.2 Hz, 2H), 1.08 (t, J=7.2 Hz, 6H).

Step 3: Ethyl 4-oxo-1,4-dihydro-1,7-naphthyridine-7-oxide-3-carboxylate

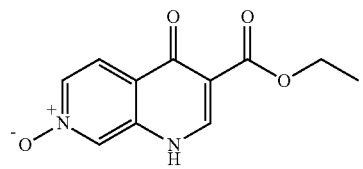

To a refluxing solution of Dowtherm A (120 mL) was added 3-(3-ethoxy-2-(ethoxycarbonyl)-3-oxoprop-1-enylamino)pyridine 1-oxide (4.0 g, 14.2 mmol), then the mixture was stirred at reflux for 15 min and cooled rapidly to room temperature and hexane (200 mL) was added. The precipitate was collected by filtration, washed with hot ethanol (20 mL) and then with hexane (50 mL) and dried in vacuo to afford the title compound (1.55 g), which was used in next step without further purification. $^1$H NMR (300 MHz, DMSO) δ 12.36 (br s, 1H), 8.64 (s, 1H), 8.59 (s, 1H), 8.11 (d, J=1.2 Hz, 1H), 7.97 (d, J=5.1 Hz, 1H), 4.22 (q, J=5.4, 2 H), 1.29 (t, J=5.4 Hz, 3H).

Step 4: 4-Oxo-1,4-dihydro-1,7-naphthyridine-3-carboxylic acid

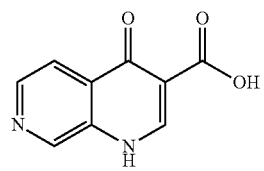 [SMILES: O=C(O)c1c[nH]c2cnccc2c1=O]

A suspension of ethyl 4-oxo-1,4-dihydro-1,7-naphthyridine-7-oxide-3-carboxylate (700 mg, 2.98 mmol) and iron powder (500 mg) in acetic acid (12 mL) and pyridine (2.5 mL) was stirred for 2 h at room temperature. The solvent was evaporated in vacuo and the residue was stirred in water (15 mL) and was added 40% NaOH to make the solution slightly basic (~5 mL). The mixture was heated at 100° C. for 30 min. Reaction mixture was cooled and filtered and the solid was washed with water (5 mL). The filtrate was acidified using 1N aq. hydrochloric acid. A precipitate was formed and removed by filtration, washed with cold water and dried under vacuum to afford the title compound (193 mg). $^1$H NMR (300 MHz, DMSO) δ 14.80 (br, 1H), 13.6 (br s, 1H), 9.26 (s, 1H), 9.04 (s, 1H), 8.72 (m, 1H), 8.13 (s, 1H).

B. Preparation of Amines

Preparation 3: 3-tert-Butyl-1H-indol-6-ylamine

Step 1: 3-tert-Butyl-6-nitro-1H-indole

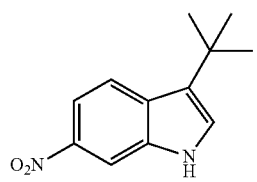

To a mixture of 6-nitroindole (1 g, 6.2 mmol), zinc triflate (2.06 g, 5.7 mmol) and TBAI (1.7 g, 5.16 mmol) in anhydrous toluene (11 mL) was added DIEA (1.47 g, 11.4 mmol) at room temperature under nitrogen. The reaction mixture was stirred for 10 min at 120° C., followed by addition of t-butyl bromide (0.707 g, 5.16 mmol). The resulting mixture was stirred for 45 min at 120° C. The solid was filtered off and the filtrate was concentrated to dryness and purified by column chromatography on silica gel (Pet.Ether./EtOAc 20:1) to give 3-tert-butyl-6-nitro-1H-indole as a yellow solid (0.25 g). $^1$H NMR (CDCl$_3$) δ 8.32 (d, J=2.1 Hz, 1H), 8.00 (dd, J=2.1, 14.4 Hz, 1H), 7.85 (d, J=8.7 Hz, 1H), 7.25 (s, 1H), 1.46 (s, 9H).

Step 2: 3-tert-Butyl-1H-indol-6-ylamine

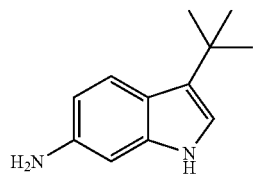 [SMILES: CC(C)(C)c1c[nH]c2cc([N+](=O)[O-])ccc12]

A suspension of 3-tert-butyl-6-nitro-1H-indole (3.0 g, 13.7 mmol) and Raney Ni (0.5 g) in ethanol was stirred at room temperature under H$_2$ (1 atm) for 3 h. The catalyst was filtered off and the filtrate was concentrated to dryness. The residue was purified by column chromatography on silica gel (Pet.Ether./EtOAc 4:1) to give 3-tert-butyl-1H-indol-6-ylamine (2.0 g) as a gray solid. $^1$H NMR (CDCl$_3$): δ 7.58 (m, 2H), 6.73 (d, J=1.2 Hz, 1H), 6.66 (s, 1H), 6.57 (dd, J=0.8, 8.6 Hz, 1H), 3.60 (br s, 2H), 1.42 (s, 9H).

Preparation 4: N-(5-tert-butyl-1H-indol-6-yl)-4-oxo-1,4-dihydro-1,7 naphthyridine-3-carboxamide Step 1: 2-Bromo-4-tert-butyl-phenylamine

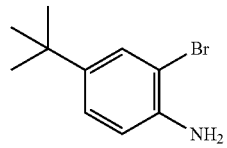

To a solution of 4-tert-butyl-phenylamine (447 g, 3 mol) in DMF (500 mL) was added dropwise NBS (531 g, 3 mol) in DMF (500 mL) at room temperature. Upon completion, the reaction mixture was diluted with water and extracted with EtOAc. The organic layer was washed with water, brine, dried over Na$_2$SO$_4$ and concentrated. The crude product was directly used in the next step without further purification.

Step 2: 2-Bromo-4-tert-butyl-5-nitro-phenylamine

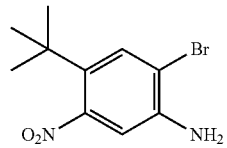

2-Bromo-4-tert-butyl-phenylamine (162 g, 0.71 mol) was added dropwise to H$_2$SO$_4$ (410 mL) at room temperature to yield a clear solution. This clear solution was then cooled down to −5 to −10° C. A solution of KNO$_3$ (82.5 g, 0.82 mol) in H$_2$SO$_4$ (410 mL) was added dropwise while the temperature was maintained between −5 to −10° C. Upon completion, the reaction mixture was poured into ice/water and extracted with EtOAc. The combined organic layers were washed with 5% Na$_2$CO$_3$ and brine, dried over Na$_2$SO$_4$ and concentrated. The residue was purified by a column chromatography (EtOAc/petroleum ether 1/10) to give 2-bromo-4-tert-butyl-5-nitro-phenylamine as a yellow solid (152 g).

Step 3: 4-tert-Butyl-5-nitro-2-trimethylsilanylethynyl-phenylamine

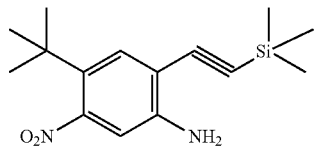 [SMILES: CC(C)(C)c1cc(C#C[Si](C)(C)C)c(N)cc1[N+](=O)[O-]]

To a mixture of 2-bromo-4-tert-butyl-5-nitro-phenylamine (27.3 g, 100 mmol) in toluene (200 mL) and water (100 mL) was added Et$_3$N (27.9 mL, 200 mmol), Pd(PPh$_3$)$_2$Cl$_2$ (2.11 g, 3 mmol), CuI (950 mg, 0.5 mmol) and trimethylsilyl acetylene (21.2 mL, 150 mmol) under a nitrogen atmosphere. The reaction mixture was heated at 70° C. in a sealed pressure flask for 2.5 h., cooled to room temperature and filtered through Celite®. The filter cake was washed with EtOAc. The combined filtrate was washed with 5% NH$_4$OH solution and water, dried over Na$_2$SO$_4$ and concentrated. The crude product was purified by column chromatography (0-10% EtOAc/petroleum ether) to provide 4-tert-butyl-5-nitro-2-trimethylsilanylethynylphenylamine as a brown viscous liquid (25 g, 81%).

Step 4: 5-tert-Butyl-6-nitro-1H-indole

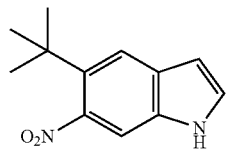

To a solution of 4-tert-butyl-5-nitro-2-trimethylsilanylethynylphenylamine (25 g, 86 mmol) in DMF (100 mL) was added CuI (8.2 g, 43 mmol) under a nitrogen atmosphere. The mixture was heated at 135° C. in a sealed pressure flask overnight, cooled down to room temperature and filtered through Celite®. The filter cake was washed with EtOAc. The combined filtrate was washed with water, dried over Na$_2$SO$_4$ and concentrated. The crude product was purified by column chromatography (10-20% EtOAc/Hexane) to provide 5-tert-butyl-6-nitro-1H-indole as a yellow solid (12.9 g).

Step 5: 5-tert-Butyl-1H-indol-6-ylamine

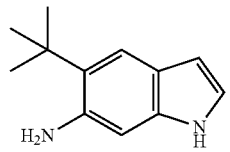

Raney Ni (3 g) was added to 5-tert-butyl-6-nitro-1H-indole (14.7 g, 67 mmol) in methanol (100 mL). The mixture was stirred under hydrogen (1 atm) at 30° C. for 3 h. The catalyst was filtered off. The filtrate was dried over Na$_2$SO$_4$ and concentrated. The crude dark brown viscous oil was purified by column chromatography (10-20% EtOAc/petroleum ether) to give 5-tert-butyl-1H-indol-6-ylamine as a gray solid (11 g).

¹H NMR (300 MHz, DMSO-d6) δ 10.3 (br s, 1H), 7.2 (s, 1H), 6.9 (m, 1H), 6.6 (s, 1H), 6.1 (m, 1H), 4.4 (br s, 2H), 1.3 (s, 9H).

Preparation 5:
5-amino-4-fluoro-2-(1-methylcyclohexyl)phenyl methyl carbonate

Step 1: 4-fluoro-2-(1-methylcyclohexyl)phenol

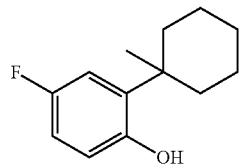

4-Fluorophenol (41.8 g, 373 mmol) and 1-methylcyclohexanol (63.8 g, 560 mmol) dissolved in 600 mL of dried CH$_2$Cl$_2$, were treated with concentrated sulfuric acid (98%, 22.3 mL, 418 mmol). The mixture was stirred at room temperature for 50 hours. The reaction mixture was then extracted by CH$_2$Cl$_2$ (250 mL×3). The organic layer was washed with saturated a.q NaHCO$_3$., dried over MgSO$_4$, and evaporated under vacuum. The residue was purified by column chromatography on silica gel to give 4-fluoro-2-(1-methylcyclohexyl)phenol as a dark green oil—47.6 g. ¹H NMR (400 MHz, CDCl$_3$) δ 7.00 (dd, J=3.2, 11.2 Hz, 1H), 6.76-6.71 (m, 1H), 6.62-6.59 (m, 1H), 5.27 (brs, 1H), 2.13-2.07 (m, 2H), 1.70-1.37 (m, 8H), 1.32 (s, 3H).

Step 2: 4-fluoro-2-(1-methylcyclohexyl)phenyl methyl carbonate

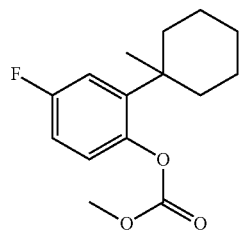 [SMILES: COC(=O)Oc1ccc(F)cc1C1(C)CCCCC1]

To a solution of 4-fluoro-2-(1-methylcyclohexyl)phenol (23.5 g, 113 mmol), TEA (31 mL, 226 mmol) and DMAP (700 mg, 5.7 mmol) in CH$_2$Cl$_2$ (250 mL) was added methyl chloroformate dropwise at 0° C. The mixture was allowed to warm to room temperature and stirred for 2 hours. The reaction mixture was poured onto crushed ice and extracted with CH$_2$Cl$_2$ (100 mL×3). The organic layer was washed with brine, dried over MgSO$_4$, evaporated under vacuum. The crude product was purified by chromatography on silica gel diluted with (hexane:ethyl acetate=100:1) to give 4-fluoro-2-(1-methylcyclohexyl)phenyl methyl carbonate as red brown oil (43.9 g, 72.1% yield). ¹H NMR (400 MHz, CDCl$_3$) δ 7.10 (dd, J=3.2, 11.2 Hz, 1H), 7.05-7.02 (m, 1H), 6.93-6.88 (m, 1H), 3.91 (s, 3H), 2.02-1.96 (m, 2H), 1.66-1.36 (m, 8H), 1.23 (s, 3H).

Step 3:
4-fluoro-2-(1-methylcyclohexyl)-5-nitrophenyl methyl carbonate

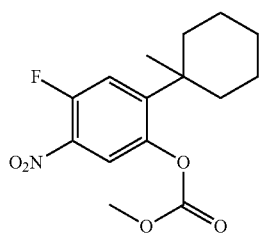 [SMILES: COC(=O)Oc1cc([N+](=O)[O-])c(F)cc1C1(C)CCCCC1]

To a solution of 4-fluoro-2-(1-methylcyclohexyl)phenyl methyl carbonate (21.5 g, 81 mmol) in 10 mL of concentrated sulfuric acid was added drop-wise to ice cold mixture of concentrated sulfuric acid (120 mL) and KNO$_3$ (8.2 g, 81 mmol) at 0° C. After addition, the reaction mixture was stirred for 15 min while warming to ambient temperature, poured onto crushed ice, extracted with ethyl acetate (120 mL×3). The organic layer was washed with brine, dried over MgSO$_4$, and evaporated under vacuum. The residue was purified by chromatography on silica gel (hexane:ethyl acetate=100:1) to give 4-fluoro-2-(1-methylcyclohexyl)-5-nitrophenyl methyl carbonate as a yellow oil (40.8 g, 81% yield). ¹H NMR (400 MHz, CDCl$_3$) δ 7.90 (d, J=6.8 Hz, 1H), 7.34 (d, J=13.2 Hz, 1H), 3.97 (s, 1H), 2.02-1.96 (m, 2H), 1.73-1.45 (m, 8H), 1.39 (s, 3H).

Step 4:
5-amino-4-fluoro-2-(1-methylcyclohexyl)phenyl methyl carbonate

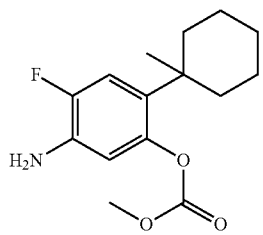

To a solution of 4-fluoro-2-(1-methylcyclohexyl)-5-nitrophenyl methyl carbonate 24.1 g, 77.5 mmol) in 220 mL of CH$_3$OH was added Pd/C 10%, 9.6 g, then ammonium formate (26.7 g, 445 mmol) was portion-wise added to the above reaction mixture at room temperature until starting material is consumed. The mixture was filtrated and the filtrate was evaporated under vacuum. The residue was purified by column chromatography on silica gel diluted with hexane:ethyl acetate=50:1 to give 5-amino-4-fluoro-2-(1-methylcyclohexyl)phenyl methyl carbonate as a red brown oil (17.9 g, 82% yield). ¹H NMR (400 MHz, CDCl₃) δ 6.99 (d, J=13.6 Hz, 1H), 6.51 (d, J=8.4 Hz, 1H), 3.89 (s, 3H), 3.43 (brs, 2H), 1.96-1.91 (m, 2H), 1.58-1.38 (m, 8H), 1.18 (s, 3H): MS m/z: 281.9 [M+H]⁺

Step 5: 2-tert-Butyl-5-amino-4-fluorophenol

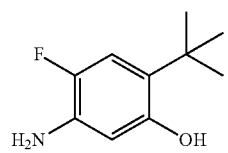

To a refluxing solution of 2-tert-butyl-4-fluoro-5-nitrophenol (400 mg, 1.88 mmol) and ammonium formate (400 mg, 6.1 mmol) in EtOH (20 mL) was added 5% Pd—C (260 mg). The mixture was refluxed for additional 1 h, cooled and filtered through Celite. The solvent was removed by evaporation to give 2-tert-butyl-5-amino-4-fluorophenol (550 mg). ¹H NMR (400 MHz, DMSO-d₆) δ 8.83 (br s, 1H), 6.66 (d, J=13.7 Hz, 1H), 6.22 (d, J=8.5 Hz, 1H), 4.74 (br s, 2H), 1.26 (s, 9H); HPLC ret. time 2.58 min, 10-99% CH₃CN, 5 min run; ESI-MS 184.0 m/z (MH⁺).

Preparation 6: (S)-4-(2-methylpyrrolidin-1-yl)-2-(trifluoromethyl)aniline

Step 1: (S)-2-methyl-1-(4-nitro-3-(trifluoromethyl)phenyl)pyrrolidine

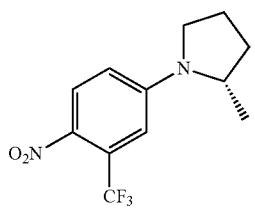 [SMILES: C[C@H]1CCCN1c1ccc(N)c(C(F)(F)F)c1]

A solution of (R)-3-methylpyrrolidine (1.000 g, 8.226 mmol), 4-fluoro-1-nitro-2-(trifluoromethyl)benzene (1.72 g, 8.226 mmol) and Et3N (2.080 g, 2.865 mL, 20.56 mmol) in ACN was heated at 80° C. for 5 hours. The reaction was cooled to RT, quenched with water, the layers separated and the aqueous layer was extracted with DCM. The combined organic layer was washed with 1M HCl to remove the unreacted amine. The organic layer was dried over Na₂SO₄, filtered and concentrated to give (S)-3-methyl-1-(4-nitro-3-(trifluoromethyl)phenyl)pyrrolidine (1.97 g, 7.184 mmol) MS 275.0 m/z (MH⁺).

Step 2: (S)-4-(2-methylpyrrolidin-1-yl)-2-(trifluoromethyl)aniline

A flask charged with (S)-3-methyl-1-(4-nitro-3-(trifluoromethyl)phenyl)pyrrolidine (1 g, 3.646 mmol) and palladium (100 mg, 0.9397 mmol) was flushed with N₂ followed by evacuating under vacuum. Methanol (10 mL) was added under inert atmosphere followed by evacuating under vacuum. The reaction placed under an atmosphere of hydrogen and the reaction was stirred overnight. Pd/C was removed by filtration and solvent was removed under reduced pressure to give (S)-4-(3-methylpyrrolidin-1-yl)-2-(trifluoromethyl)aniline (850 mg, 95%) MS 245.0 m/z (MH⁺).

Preparation 7: 3-(trifluoromethyl)-1H-indol-6-amine

Step 1: Methyl 2-(2,4-dinitrophenyl)-3,3,3-trifluoro-2-hydroxypropanoate

To a solution of 1,4-dinitroiodobenzene (2.12 g, 7.21 mmol) in anhydrous THF (11.0 mL) at −78° C. under nitrogen was added phenylmagnesium chloride (2M in THF) (4.0 mL, 8.0 mmol, 1.1 eq) dropwise. The dark red solution was stirred for 30 min at −78° C. then methyltrifluoropyruvate (0.75 mL, 8.65 mmol, 1.2 eq) was added dropwise. The reaction mixture was stirred for 30 min at −78° C. and for 2 h at room temperature. The reaction was cooled down to −10° C. and quenched by addition of 1M HCl (6 mL). The mixture was diluted with water (10 mL) and DCM (30 mL). The organic phase was separated and the aqueous phase was extracted with DCM (3×30 mL). The organic phases were combined, dried with sodium sulfate, filtered, and concentrated to dryness. The crude residue was purified by silica gel column chromatography using a gradient 0.5-30% ethyl acetate in hexanes 1.4 g of methyl 2-(2,4-dinitrophenyl)-3,3,3-trifluoro-2-hydroxypropanoate (1.34 g, 60%)

was quenched by adding very carefully 6M HCl (3.5 mL) until no more gas release was observed. The mixture was then stirred at 80° C. for 2 h. The solvent was removed under reduce pressure and the solid residue obtained was dissolved in DMF (3 mL), filtered and purified by reverse phase HPLC (10-99% ACN in water) to give 3-(trifluoromethyl)-1H-indol-6-amine (30 mg, 54%, TFA salt).

Step 2:
6-amino-3-hydroxy-3-(trifluoromethyl)indolin-2-one

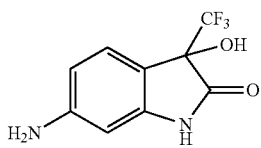 [SMILES: Nc1ccc2c(c1)NC(=O)C2(O)C(F)(F)F]

To a solution of methyl 2-(2,4-dinitrophenyl)-3,3,3-trifluoro-2-hydroxypropanoate (1.3 g, 4.01 mmol) in ethyl acetate (18 mL) was successively added pH3HCl (5.2 mL), then PdC (350 mg) in ethyl acetate (3 mL). The mixture was vigorously stirred overnight under H$_2$ (1 atm). The catalyst was filtered off through Celite and the filtrate was concentrated to dryness. The crude residue obtained was partitioned between DCM (25 mL) and aqueous saturated NaHCO$_3$ (15 mL). The organic phase was separated and the aqueous phase was extracted DCM (2×25 mL). The organic phases were combined, dried over sodium sulfate, filtered, and concentrated. The crude residue obtained was purified by silica gel column chromatography using a gradient 50-100% ethyl acetate in hexanes to give 6-amino-3-hydroxy-3-(trifluoromethyl)indolin-2-one (921 mg, 99%)

Step 3: 3-(trifluoromethyl)-1H-indol-6-amine

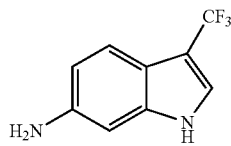 [SMILES: Nc1ccc2c(C(F)(F)F)c[nH]c2c1]

To a solution of 6-amino-3-hydroxy-3-(trifluoromethyl) indolin-2-one (58 mg, 0.25 mmol) in anhydrous THF (0.5 mL) at 0° C. was added BH$_3$.THF complex (1M in THF) (1 mL, 0.95 mmol, 4 eq) dropwise. The mixture was stirred for 5 min at 0° C. then for 3 h at room temperature. The reaction Preparation 8: (1-(4-(trifluoromethoxy)phenyl)cyclopentyl)methanamine Step 1: 1-(4-(trifluoromethoxy)phenyl)cyclopentanecarbonitrile

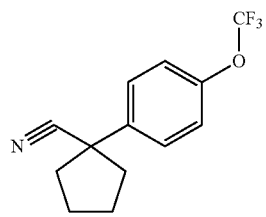 [SMILES: N#CC1(c2ccc(OC(F)(F)F)cc2)CCCC1]

To sodium hydride (600 mg, 15 mmol) in anhydrous THF (5 mL) at 0° C., was added dropwise 2-(4-(trifluoromethoxy)phenyl)acetonitrile (1006 mg, 5 mmol) and then the reaction mixture was stirred for 5 mins, followed by dibromobutane (1075 mg, 5 mmol) dropwise. The reaction mixture was heated to reflux for 16 h, then cooled to 0° C., quenched with MeOH (1 mL), diluted with EtOAC (50 mL) and washed with brine (3×50 mL). The organic layer was dried over sodium sulfate and concentrated in vacuo to give 1-(4-(trifluoromethoxy)phenyl)cyclopentanecarbonitrile as a yellow oil (905 mg, 71%) ($^1$H NMR (400 MHz, CDCl$_3$) 7.50 (dd, J=2.1, 6.7 Hz, 2H), 7.25 (d, J=8.2 Hz, 2H), 2.53-2.49 (m, 2H), 2.10-1.97 (m, 6H)

Step 2: (1-(4-(trifluoromethoxy)phenyl)cyclopentyl)methanamine

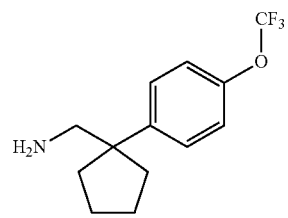 [SMILES: NCC1(c2ccc(OC(F)(F)F)cc2)CCCC1]

To lithium aluminium hydride (379 mg, 10 mmol) in Et$_2$O (10 mL) was added dropwise a solution of 1-(4-(trifluoromethoxy)phenyl)cyclopentanecarbonitrile (905 mg, 4 mmol) in Et$_2$O (5 mL) at 0° C. The reaction mixture was stirred at room temperature under an atmosphere of nitrogen for 16 h and then quenched with saturated sodium sulfate solution (3 mL) and extracted with Et$_2$O. The organic layer was dried with sodium sulfate and evaporated in vacuo to give (1-(4-(trifluoromethoxy)phenyl)cyclopentyl)methanamine as an oil (810 mg, 77%).

C. Preparation of Naphthyridine Carboxamides

Preparation 9: N-(5-tert-butyl-1H-indol-6-yl)-4-oxo-1,4-dihydro-1,7-naphthyridine-3-carboxamide

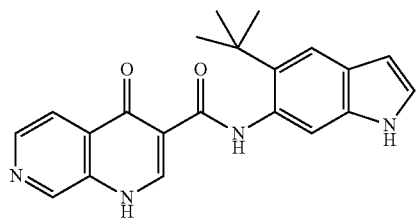 [SMILES: CC(C)(C)c1cc2cc[nH]c2cc1NC(=O)c1c[nH]c2cnccc2c1=O]

To 4-oxo-1,4-dihydro-1,7-naphthyridine-3-carboxylic acid (48 mg, 0.25 mmol), 5-tert-butyl-1H-indol-6-amine (48 mg, 0.25 mmol) in DMF (1 mL) was added HATU (106 mg, 0.28 mmol), followed by triethylamine (106 μL, 0.76 mmol) and the reaction mixture was heated at 80° C. for 16 h. The reaction mixture was then purified by reverse phase HPLC 10-99% ACN in water to give N-(5-tert-butyl-1H-indol-6-yl)-4-oxo-1,4-dihydro-1,7-naphthyridine-3-carboxamide. MS m/z: 361.5 [M+H]$^+$ Analytical data for the compounds of Table 1 is provided in Table 2.

TABLE 2

| Cmpd # | LC/MS M + 1 | LC/RT min | NMR |
|---|---|---|---|
| 1 | 356 | 2.53 | — |
| 2 | 370 | 2.55 | — |
| 3 | 308.2 | 2.51 | — |
| 4 | 308.2 | 2.45 | — |
| 5 | 342 | 2.51 | — |
| 6 | 305.5 | 2.19 | — |
| 7 | 403.5 | 1.36 | — |
| 8 | 432.06 | 1.45 | — |
| 9 | 394.3 | 1.81 | — |
| 10 | 361.5 | 1.48 | — |
| 11 | 403.1 | 1.55 | — |
| 12 | 417.2 | 1.39 | — |
| 13 | 396.2 | 1.84 | — |
| 14 | 373 | 1.44 | $^1$H NMR (300.0 MHz, DMSO-d6) δ 6.59 (s, 1H), 7.51 (s, 1H), 7.98 (s, 1H), 8.16 (d, J = 3.96 Hz, 1H), 8.32 (s, 1H), 8.65 (d, J = 4.0 Hz, 1H), 9.02 (d, J = 4.4 Hz, 1H), 9.22 (s, 1H), 11.54 (s, 1H). 12.23 (s, 1H), 13.37 (d, J = 4.4 Hz, 1H). |
| 15 | 387.2 | 1.36 | |
| 16 | 373 | 1.43 | |
| 17 | 410.2 | 1.82 | |
| 18 | 445.5 | 1.72 | $^1$H NMR (400.0 MHz, DMSO-d6) δ13.31 (s, 1H), 12.09 (s, 1H), 9.20 (s, 1H), 9.00 (s, 1H), 8.65 (d, J = 4.5 Hz, 1H), 8.15 (d, J = 5.3 Hz, 1H), 8.00 (d, J = 9.1 Hz, 1H), 7.24 (dd, J = 2.9, 9.1 Hz, 1H), 7.12 (d, J = 2.8 Hz, 1H), 3.14 (t, J = 5.6 Hz, 2H), 2.90 (s, 2H), 1.67 (m, 2H), 1.36 (m, 2H) and 0.98 (s, 6H) ppm |

It is noted that "—" indicates that no data is available.

Assays for Detecting and Measuring ΔF508-CFTR Potentiation Properties of Compounds Membrane Potential Optical Methods for Assaying ΔF508-CFTR Modulation Properties of Compounds The optical membrane potential assay utilized voltage-sensitive FRET sensors described by Gonzalez and Tsien (See, Gonzalez, J. E. and R. Y. Tsien (1995) "Voltage sensing by fluorescence resonance energy transfer in single cells" Biophys J 69(4): 1272-80, and Gonzalez, J. E. and R. Y. Tsien (1997) "Improved indicators of cell membrane potential that use fluorescence resonance energy transfer" Chem Biol 4(4): 269-77) in combination with instrumentation for measuring fluorescence changes such as the Voltage/Ion Probe Reader (VIPR) (See, Gonzalez, J. E., K. Oades, et al. (1999) "Cell-based assays and instrumentation for screening ion-channel targets" Drug Discov Today 4(9): 431-439).

These voltage sensitive assays are based on the change in fluorescence resonant energy transfer (FRET) between the membrane-soluble, voltage-sensitive dye, DiSBAC$_2$(3), and a fluorescent phospholipid, CC2-DMPE, which is attached to the outer leaflet of the plasma membrane and acts as a FRET donor. Changes in membrane potential ($V_m$) cause the negatively charged DiSBAC$_2$(3) to redistribute across the plasma membrane and the amount of energy transfer from CC2-DMPE changes accordingly. The changes in fluorescence emission were monitored using VIPR™ II, which is an integrated liquid handler and fluorescent detector designed to conduct cell-based screens in 96- or 384-well microtiter plates.

Identification of Potentiator Compounds

Typical protocol utilized a basolateral to apical membrane Cl$^-$ concentration gradient. To set up this gradient, normal ringers was used on the basolateral membrane and was permeabilized with nystatin (360 μg/ml), whereas apical NaCl was replaced by equimolar sodium gluconate (titrated to pH 7.4 with NaOH) to give a large Cl$^-$ concentration gradient across the epithelium. All experiments were performed 30 min after nystatin permeabilization. Forskolin (10 μM) and all test compounds were added to both sides of the cell culture inserts. The efficacy of the putative ΔF508-CFTR potentiators was compared to that of the known potentiator, genistein.

| | Solutions |
|---|---|
| Basolateral solution (in mM): | NaCl (135), CaCl$_2$ (1.2), MgCl$_2$ (1.2), K$_2$HPO$_4$ (2.4), KHPO$_4$ (0.6), N-2-hydroxyethylpiperazine-N'-2-ethanesulfonic acid (HEPES) (10), and dextrose (10). The solution was titrated to pH 7.4 with NaOH. |
| Apical solution (in mM): | Same as basolateral solution with NaCl replaced with Na Gluconate (135). |

Cell Culture

Fisher rat epithelial (FRT) cells expressing ΔF508-CFTR (FRTΔ$^{F508-CFTR}$) were used for Ussing chamber experiments for the putative ΔF508-CFTR modulators identified from our optical assays. The cells were cultured on Costar Snapwell cell culture inserts and cultured for five days at 37° C. and 5% CO$_2$ in Coon's modified Ham's F-12 medium supplemented with 5% fetal calf serum, 100 U/ml penicillin, and 100 μg/ml streptomycin. Prior to use for characterizing the potentiator activity of compounds, the cells were incubated at 27° C. for 16-48 hrs to correct for the ΔF508-CFTR. To determine the activity of corrections compounds, the cells were incubated at 27° C. or 37° C. with and without the compounds for 24 hours.

2. Whole-Cell Recordings

The macroscopic ΔF508-CFTR current ($I_{\Delta F508}$) in temperature- and test compound-corrected NIH3T3 cells stably expressing ΔF508-CFTR were monitored using the perforated-patch, whole-cell recording. Briefly, voltage-clamp recordings of $I_{\Delta F508}$ were performed at room temperature using an Axopatch 200B patch-clamp amplifier (Axon Instruments Inc., Foster City, Calif.). All recordings were acquired at a sampling frequency of 10 kHz and low-pass filtered at 1 kHz. Pipettes had a resistance of 5-6 MΩ when filled with the intracellular solution. Under these recording conditions, the calculated reversal potential for Cl⁻ ($E_{Cl}$) at room temperature was −28 mV. All recordings had a seal resistance >20 GΩ and a series resistance <15 MΩ. Pulse generation, data acquisition, and analysis were performed using a PC equipped with a Digidata 1320 A/D interface in conjunction with Clampex 8 (Axon Instruments Inc.). The bath contained <250 μl of saline and was continuously perifused at a rate of 2 ml/min using a gravity-driven perfusion system.

Compounds of the invention are useful as modulators of ATP binding cassette transporters. Table 3 below illustrates the $EC_{50}$ and relative efficacy of certain embodiments in Table 1.

In Table 3 below, the following meanings apply:
$EC_{50}$: "+++" means <10 uM; "++" means between 10 uM to 25 uM; "+" means between 25 uM to 60 uM.
% Efficacy: "+" means <25%; "++" means between 25% to 100%; "+++" means >100%.

TABLE 3

| Cmpd # | $EC_{50}$ (μm) | % Efficacy |
|---|---|---|
| 1 | +++ | +++ |
| 2 | +++ | ++ |
| 3 | +++ | ++ |
| 4 | +++ | ++ |
| 5 | +++ | ++ |
| 6 | +++ | + |
| 7 | +++ | ++ |
| 8 | +++ | ++ |
| 9 | +++ | ++ |
| 10 | +++ | ++ |
| 11 | +++ | ++ |
| 12 | +++ | ++ |
| 13 | +++ | ++ |
| 14 | +++ | ++ |
| 15 | +++ | ++ |
| 16 | +++ | ++ |
| 17 | ++ | + |
| 18 | +++ | ++ |

What is claimed is:

1. A method of modulating CFTR activity comprising the step of contacting said CFTR with a compound of formula (VA):

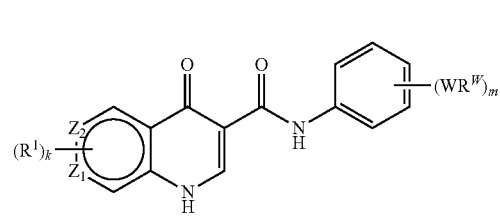

IVA or a pharmaceutically acceptable salt or tautomer thereof, wherein:
k is 0 or 1;
Each $R^1$ is independently H, halo or $C_{1-3}$ alkyl;
Each W is a bond or a $C_{1-6}$ straight or branched aliphatic chain wherein up to 2 of the carbon units are optionally and independently replaced by —CO—, —CS—, —COCO—, —CONR'—, —CONR'NR'—, —CO₂—, —OCO—, —NR'CO₂—, —O—, —NR'CONR'—, —OCONR'—, —NR'NR'—, —NR'NR'CO—, —NR'CO—, —S—, —SO, —SO₂—, —NR'—, —SO₂NR'—, —NR'SO₇—, or —NR'SO₂NR'—; and $R^W$ is independently R', halo, —NO₂, —CN, —CF₃, or —OCF₃;
m is 0-5;
Each R' is hydrogen or a group selected from a $C_{1-8}$ aliphatic, a 3-8 membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or two occurrences of R' are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur; and
Each of $Z_1$ or $Z_2$ is independently —CH—, —$CR^1$—, or N, and at least one of $Z_1$ or $Z_2$ is N.

2. A method of treating or lessening the severity of a disease in a patient, wherein said disease is selected from cystic fibrosis, hereditary emphysema, COPD, or dry-eye disease, said method comprising the step of administering to said patient an effective amount of a compound of formula IVA according to claim 1.

3. The method according to claim 1, wherein $R^1$ is hydrogen or $C_{1-3}$ alkyl.

4. The method according to claim 3, wherein $R^1$ is hydrogen or —CH₃.

5. The method according to claim 1, wherein said compound has formula VA-1,

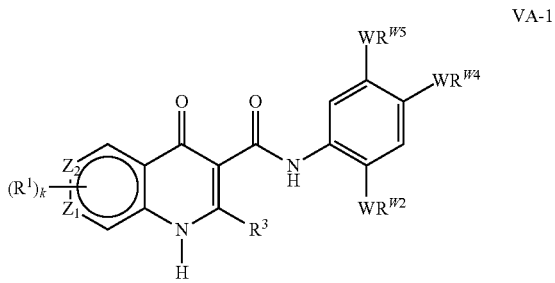

VA-1 wherein each of $WR^{W2}$ and $WR^{W4}$ is independently selected from hydrogen, CN, CF₃, OCF₃, halo, C1-C6 straight or branched alkyl, 3-12 membered cycloaliphatic, phenyl, C5-C10 heteroaryl or C3-C7 heterocyclic, wherein said heteroaryl or heterocyclic has up to 3 heteroatoms selected from O, S, or N, wherein said $WR^{W2}$ and $WR^{W4}$ is independently and optionally substituted with up to three substituents selected from —OR', —CF₃, —OCF₃, SR', S(O)R', SO₂R', —SCF₃, halo, CN, —COOR', —COR', —O(CH₂)₂N(R')(R'), —O(CH₂)N(R')(R'), —CON(R')(R'), —(CH₂)₂OR', —(CH₂)OR', CH₂CN, phenyl or phenoxy, —N(R')(R'), —NR'C(O)OR', —NR'C(O)R', —(CH₂)₂N(R')(R'), or —(CH₂)N(R')(R'); and
$WR^{W5}$ is selected from hydrogen, halo, —OH, NH₂, CN, CHF₂, NHR', N(R)₂, —NHC(O)R', —NHC(O)OR', NHSO$_2$R', —OR', CH$_2$OH, CH$_2$N(R')$_2$, C(O)OR', C(O)N(R')$_2$, SO$_2$NHR', SO$_2$N(R')$_2$, OSO$_2$N(R')$_2$, OSO$_2$CF$_3$, or CH$_2$NHC(O)OR'.

6. The method according to claim 5, wherein said compound formula V-A-3:

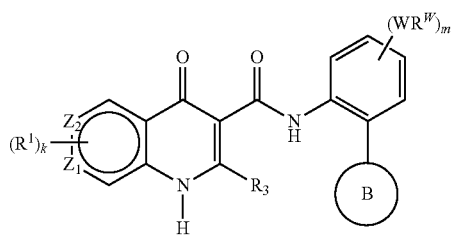

V-A-3 wherein: ring B is a 5-7 membered monocyclic or bicyclic, heterocyclic or heteroaryl ring optionally substituted with up to n occurrences of -Q-R$^Q$;

Q is W;
R$^Q$ is R$^W$;
m is 0-4; and
n is 0-4.

7. The method according to claim 1, wherein said compound is selected from:

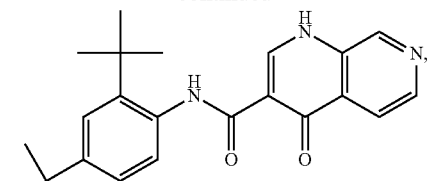

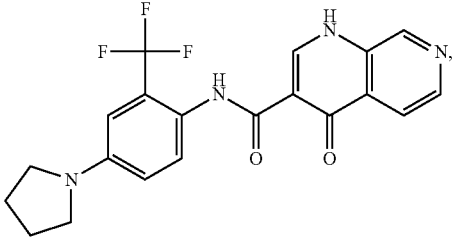

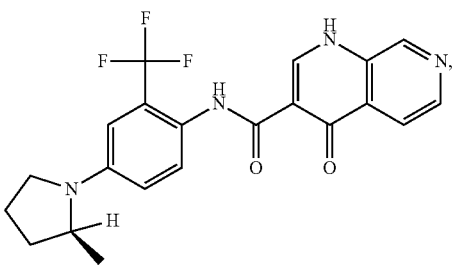

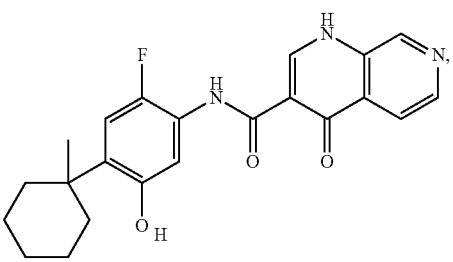

-continued

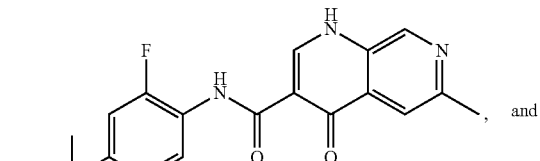

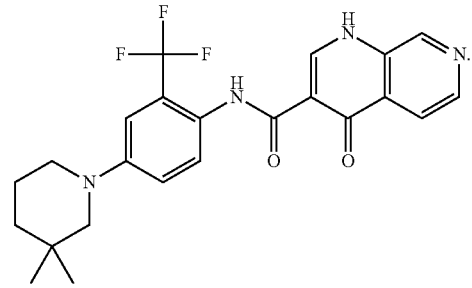

, and

* * * * *